US008492344B2

(12) United States Patent
Ostrov et al.

(10) Patent No.: US 8,492,344 B2
(45) Date of Patent: Jul. 23, 2013

(54) PDK INHIBITOR COMPOUNDS AND METHODS OF USE THEREOF

(75) Inventors: David A. Ostrov, Gainesville, FL (US); Peter Stacpoole, Gainesville, FL (US); Arun Srivastava, Gainesville, FL (US)

(73) Assignee: University of Florida Research Foundation, Gainesville, FL (US)

( * ) Notice: Subject to any disclaimer, the term of this patent is extended or adjusted under 35 U.S.C. 154(b) by 0 days.

(21) Appl. No.: 13/061,870

(22) PCT Filed: Sep. 1, 2009

(86) PCT No.: PCT/US2009/004949
§ 371 (c)(1),
(2), (4) Date: Jul. 1, 2011

(87) PCT Pub. No.: WO2010/027458
PCT Pub. Date: Mar. 11, 2010

(65) Prior Publication Data
US 2012/0004284 A1 Jan. 5, 2012

Related U.S. Application Data

(60) Provisional application No. 61/190,844, filed on Sep. 2, 2008.

(51) Int. Cl.
*A61P 35/00* (2006.01)

(52) U.S. Cl.
USPC ....................................... 514/19.3

(58) Field of Classification Search
None
See application file for complete search history.

(56) References Cited

U.S. PATENT DOCUMENTS

| 2004/0058425 | A1* | 3/2004 | Knoechel et al. | 435/194 |
| 2007/0212360 | A1* | 9/2007 | Denko et al. | 424/155.1 |

FOREIGN PATENT DOCUMENTS

WO  WO 2006/133489  * 12/2006

OTHER PUBLICATIONS

Knoechel et al., "Regulatory Roles of the N-Terminal Domain Based on Crystal Structures of Human Pyruvate Dehydrogenase Kinase 2 Containing Physiological and Synthetic Ligands", Biochemistry 2006, 45, 402-415.*
Roche et al., "Pyruvate dehydrogenase kinase regulatory mechanisms and inhibition in treating diabetes, heart ischemia, and cancer", Cell. Mol. Life Sci. 64 (2007) 830-849.*
Klebe, G., "Foundation review: Virtual ligand screening: strategies, perspectives and limitations", Drug Discovery Today_vol. 11, Nos. 13-14 , Jul. 2006.*
Owen et al., "Gene Therapy for Pyruvate Dehydrogenase E1-alpha Deficiency Using Recombinant Adeno-Associated Virus 2 (rAAV2) Vectorss", Molecular Therapy, vol. 6, No. 3, Sep. 2002.*
Han et al., "A combined therapeutic approach for pyruvate dehydrogenase deficiency using self-complementary adeno-associated virus serotype-specific vectors and dichloroacetate", Molecular Genetics and Metabolism 93 (2008) 381-387.*
Gura, T., "Cancer Models Cancer Models Systems for Identifying New Drugs Are Often Faulty", Science, v. 278, pp. 1041-1042.*
Dermer G.B., Bio/Technology, 1994, 12:320.*

* cited by examiner

*Primary Examiner* — Suzanne M Noakes
(74) *Attorney, Agent, or Firm* — Edwards Wildman Palmer LLP; Jeffrey D. Hsi

(57) ABSTRACT

The invention relates to methods of treating or preventing acquired or congenital mitochondrial diseases or disorders, including treating cell proliferation related disorders or diseases, such as cancer. The invention further relates to pharmaceutical compositions for treating such disorders or diseases.

11 Claims, 5 Drawing Sheets

SEQUENCE LISTING

<160> NUMBER OF SEQ ID NOS: 3

<210> SEQ ID NO 1
<211> LENGTH: 2349
<212> TYPE: DNA
<213> ORGANISM: Mus musculus

<400> SEQUENCE: 1

```
ctgtattgta catactttca ataaatgtta agatgttgtt atttttttct ttaaaaacga      60
aaaggtagaa gaaagaatga tgtcattttg ctccctccct ccttccctcc tgcctgccct     120
tcctccttct cctctttcc tcctctccac cgcccctcat tttgaggcca aagagaccac     180
aaactgactg agaataggat tcaagtccgg ctcctacaaa cctcaatgcc tagtgtctga     240
gattacaggt atgtgtggca cagttactgt ctgagtttag aggtgctggg atggaaccca     300
aaagctctgc acagtaggct atgtccctac cctgccagga cttttttgag ttgtacaggg     360
aaaagacact cagttgctgt gtgagtggca accatgatgt taaataggag gaaagtgtgg     420
gagatcctcc ctttccagtt agaagcatca gaggagcagg ccccgtgggc gtggcttcca     480
gcttgctgac gtaggcaacg cgtttgcatc ccgttattgt tgcatcagag gagctcggca     540
gccatcttaa aagccactga gtgatcgttg ggagccgagc cgctaccgtt gtgcctcgcg     600
tttctccatg aggaaaatgc tgaccgctgt gctgtctcac gtattttcgg gaatggtcca     660
aaagccagct ctcagaggac tgctgtcatc tctgaagttc tccaacgacg ccacctgtga     720
cattaagaaa tgtgacctgt accggctgga ggagggccca ccgacctcca ccgtgctcac     780
ccgagccgag gccctcaagt actaccggac catgcaggta attcggcgca tggagttgaa     840
ggccgaccag ctgtataagc agaaattcat ccgtggtttc tgtcacctgt gtgatgggca     900
ggaagcctgc tgcgtggggc tggaggcagg gataaatccc acggatcacg tcatcacgtc     960
ctaccgggct catggcttct gctacacgcg aggactgtcc gtgaagtcca ttctcgccga    1020
gctgactgga cgcaaaggag gctgtgctaa aggcaaggga ggctccatgc acatgtacgg    1080
caagaacttc tacggtggca atggcattgt tggggcccag gtaccctgg gagctggtgt    1140 ggcttttgcc tgtaaatacc tgaagaatgg tcaggtctgc ttggctttgt acggcgatgg    1200
tgcggctaac caagggcagg tattcgaagc atacaatatg tcagccttgt ggaaattacc    1260
ctgtgttttc atctgtgaga ataacctcta tggaatggga acctccaacg agagatcagc    1320
agccagtact gattaccaca agaaaggttt tattatcccc ggactgaggg tgaatgggat    1380
```

```
ggatattctc tgtgttcggg aggcaaccaa gtttgcagct gatcactgca gatctggaaa      1440 gggcccatt gtgatggagc tgcagaccta ccgttatcat ggacacagta tgagcgaccc       1500
agggatcagt tatcgttcac gagaagaagt tcataacgtg agaagtaaga gtgatcctat      1560
aatgctgctc cgagagagaa ttatcagcaa caacctcagc aatattgaag aattgaaaga      1620
aattgatgca gatgtgaaga aagaggtgga ggacgcagct cagtttgcta cgactgatcc      1680
agaaccagct gtggaagata tagccaatta cctctaccac caagatccac cttttgaagt      1740
ccgtggtgca cataagtggc tcaagtataa gtcccacagt tagatagatg ttacctatac      1800
atttgttaaa tttttttttca gtgggacatt tatggtgtac tctaggaaac ttcaactttg     1860
ttaaggagga ataaataaaa cgacattgca gacaaaagtc ttataaacct ttataaagat     1920
agattcctga gttattaagg agattagaag atataaattt gtttaaagga gatgttccac     1980
tttctgtttt aacattaaaa gcattgtgtt gcatactact atgaatatct tttagactat     2040
ttcaaattta taaattata atagaaaaaa cgggttaaat tccccaattt ggcatagtag      2100
tttcatttgg ttttagtttt gaaataaata ctttatttta aaagaagtag attttttgatt   2160 ttttcttctt ctttgatgag tttgtcaaaa attaaaagtg aggaggatgg tttcaattct     2220
gtccccgccc cccctcacc aaatacctga ttatgttccc ctttcccct ccatgtccaa       2280 tctctgaccc aggttcctcc ctccctctgt ccctgtggt tgatttttcc tcctaagtag      2340
gattcaggc                                                             2349

<210> SEQ ID NO 2
<211> LENGTH: 1574
<212> TYPE: DNA
<213> ORGANISM: Rattus norvegicus

<400> SEQUENCE: 2
ggtcgttgga agccgctacg gttgtgcctc acgtttctcc atgaggaaaa tgctggccac       60
tgtgctgtct caagtatttt caggaatggt ccagaagcca gctctcaggg gactgctgtc     120
atctcttaag ttctccaacg acgccacctg tgacatcaag aaatgcgact tgtacctgtt     180
ggaacagggc ccccccacct ccactgtgct caccagagag gaggccctga atactaccg      240 gaacatgcag gtaattcggc gcatggagtt gaaggccgac cagctgtata gcagaaatt      300 catccgtggt ttctgtcacc tgtgtgatgg gcaggaagcc tgcaatgtgg ggctggaggc      360
agggataaat cccacagacc acatcatcac gtcctacaga gctcatggct tgtgctacac      420
gaggggactg tcagtgaagt ccattctcgc agagctgact ggacgcaaag gaggctgtgc      480
taaaggcaag ggaggctcta tgcacatgta cgccaagaac ttctatgggg gcaatggcat      540
tgttggggca caggtacccc tgggagctgg tgtggctctc gcctgtaaat acctgaagaa      600
tggtcagatc tgcttggctt tgtatggcga tggtgcggct aaccaagggc aggtatttga      660
agcttacaat atgtcagcct tgtggaaatt accctgtgtt ttcatctgtg agaataaccg      720
ctatggaatg ggaacagcta ttgagagatc agcagccagt actgattacc acaagaaagg      780
ctttgttatc cctggactga gggtgaatgg gatggatatt tcagtgttc gtgaggcgac       840 caagtttgca gctgatcact gcagatccgg aaaggggccc attgtgatgg agttgcagac      900
ataccgttat catggacaca gtatgagcga tccagggatc agttatcgta cacgagaaga      960
agttcagaac gtgaggagta agagtgatcc aataatgctt ctccgagaga gaatgataag     1020
caacaacctc agcagtgttg aagaattgaa agaaattgat gcagatgtga agaaagaagt     1080
cgaggaagca gctcagtttg ctacaactga tccagaacca cctctggaag atttagccaa     1140
```

| | |
|---|---|
| ttacctctac caccaaaatc caccatttga agtccgtggt gcacataaat ggctgaagtt | 1200 |
| taagtctgtc agttagagat ttgttaaaat tcttcagtgg gacatttatg gtgaacttta | 1260 |
| ggacatttt caacattgct aatgaagaaa aaataaaaca gctttacaga caaaagtctt | 1320 |
| ataagcattt ataagatac attcttgggt cctaaaggaa attagaagat aaaaatttgt | 1380 |
| ttagagatgt tccactttct gttttaacat tgtattgcaa atagtatgaa tattttttag | 1440 |
| aatattttaa atatataaaa ttataatagg aaaaacaggt taaattcccc aatttgtcat | 1500 |
| aatagtttca tttgaatttt agttttgaaa taaacactta aagaagtaa aaaaaaaaaa | 1560 |
| aaaaaaaaaa aaaa | 1574 |

<210> SEQ ID NO 3
<211> LENGTH: 3364
<212> TYPE: DNA
<213> ORGANISM: Homo sapiens

<400> SEQUENCE: 3

| | |
|---|---|
| agcgcatgac gttattacga ctctgtcacg ccgcggtgcg actgaggcgt ggcgtctgct | 60 |
| ggggcacctg aaggagactt gggggcaccc gcgtcgtgcc tcctgggttg tgaggagtcg | 120 |
| ccgctgccgc cactgcctgt gcttcatgag gaagatgctc gccgccgtct cccgcgtgct | 180 |
| gtctggcgct tctcagaagc cggcaagcag agtgctggta gcatcccgta attttgcaaa | 240 |
| tgatgctaca tttgaaatta gaaatgtga ccttcaccgg ctggaagaag ccctcctgt | 300 |
| cacaacagtg ctcaccaggg aggatgggct caaatactac aggatgatgc agactgtacg | 360 |
| ccgaatggag ttgaaagcag atcagctgta taaacagaaa attattcgtg gtttctgtca | 420 |
| cttgtgtgat ggtcaggaag cttgctgtgt gggcctggag gccggcatca cccccacaga | 480 |
| ccatctcatc acagcctacc gggctcacgg ctttactttc acccggggcc tttccgtccg | 540 |
| agaaattctc gcagagctta caggacgaaa aggaggttgt gctaaaggga aggaggatc | 600 |
| gatgcacatg tatgccaaga acttctacgg gggcaatggc atcgtggag cgcaggtgcc | 660 |
| cctgggcgct gggattgctc tagcctgtaa gtataatgga aagatgagg tctgcctgac | 720 |
| tttatatggc gatggtgctg ctaaccaggg ccagatattc gaagcttaca acatggcagc | 780 |
| tttgtggaaa ttccttgta ttttcatctg tgagaataat cgctatggaa tgggaacgtc | 840 |
| tgttgagaga gcggcagcca gcactgatta ctacaagaga ggcgatttca ttcctgggct | 900 |
| gagagtggat ggaatggata tcctgtgcgt ccgagaggca acaaggtttg ctgctgccta | 960 |
| ttgtagatct gggaagggc ccatcctgat ggagctgcag acttaccgtt accacggaca | 1020 |
| cagtatgagt gaccctggag tcagttaccg tacacgagaa gaaattcagg aagtaagaag | 1080 |
| taagagtgac cctattatgc ttctcaagga caggatggtg aacagcaatc ttgccagtgt | 1140 |
| ggaagaacta aaggaaattg atgtggaagt gaggaaggag attgaggatg ctgcccagtt | 1200 |
| tgccacggcc gatcctgagc cacctttgga agagctgggc taccacatct actccagcga | 1260 |
| cccacctttt gaagttcgtg gtgccaatca gtggatcaag tttaagtcag tcagttaagg | 1320 |
| ggaggagaag gagaggttat accttcaggg ggctaccaga cagtgttctc aacttggtta | 1380 |
| aggaggaaga aaacccagtc aatgaaattc aatgaaattc ttggaaactt ccattaagtg | 1440 |
| tgtagattga gcaggtagta attgcatgca gtttgtacat tagtgcatta aaagatgaat | 1500 |
| tattgagtgc ttaaagatta ttttgactt aaaatagtat actttgaaca aatactctaa | 1560 |
| ttatgaaaag gaagaacaat tccttgtatg cctgttccc ctgccccag ccacttttt | 1620 |
| gggaggagac cattatggcg gggcccctca cagcattcta ccaaccatag cacccacccc | 1680 |

-continued

```
gagcagcgct ggtgctgcag cctgttcgcg ctgaccattt ctctacaaga tacaatattt    1740
attatcaggc aagaggacag ttccatttta aaataagact tttgtaatca ttccaatttt    1800
gtaatcattt caaaggccac ataacttagt tttctctact tacacattca gtataaatat    1860
gaagctattt tctgttcata tcaaacatta actacaaggc acattcgtat cagttttgtg    1920
tttctcaaat tgaagtacca taccagttct gaggcagtgt cccagcttcc atgtttgtta    1980
aatacccctt gtttgtttca ccattccagc aagtgctgaa gggtgtactt tttttgagac    2040
agggtcgggc tctgttgccc aggctggagt gcagtggtgt gatcatggct cactgcagcc    2100
tccacacctc ctgggctcaa gcaatcctcc cacctcagcc tcctgcatag ctgggactac    2160
aagtgaattt cctaatattc cgggaggtca aaaccaaggc tcactgtttt cacaatacac    2220
acagttctat gtttataaat aacaggtttc aaaagaaact caggacagta tttaaaacaa    2280
gttcttaaac tattaattga acaatggcat ttttaaatat gtaaacacag cggaattcgt    2340
gtatacacta acagaagctt taacaaaaca tgtagcgtgg tgggacactc tgccacagct    2400
tagctgattg gtatcaagcc ttgtctttgg tttctgaggc ctcctgagcc cttctgtact    2460
gggagaccgc actccagagt ctgcagagga gaccacccct gggaaacaaa cacagctgtc    2520
ttcagagtca gtgcttcaag ccaacagagc ttaaaactgc agtccctaat ttaaaaacct    2580
aatgaaaata aaaacattct cctcacatat ggaggtgacg ctcgtgtccc agcagtagta    2640
ggacatggcc ttagaggtac gtacctgcag agagctggct atttcaaatg actcgggaac    2700
aagaaggcag gctgcagttt aaagaagggg gtgggtccag cgtgcaggca cgcttgccat    2760
gtgcctccac ccactcccag ccaggcatta atggcaggag attggccagc tcttctctgt    2820
cacattccta tttctgactt ctgcctggct ttcagtttct gccccacctt ggcttttttcc   2880 cagcttgaac ctaatagaac tccagagttt gggggggaggc ccagcccttt gttttctgct   2940
cttgaagcat attcacacat aaaaagttgt attctcttat acaaactgtt ttgaggctct    3000
taccgtagtc gaaggtatct tagatcttcc ttagtgatct cattaagaat atccgaaagt    3060
gtataaccct cttcaacaat ctgaaacaaa gatcagatcc ttaagagctg agcagctgtg    3120
taacaacagc ataagaattt ctttgttgta aatttacctt ttcaattgtc tttgcatcag    3180
ctccttgcag ccgcaaccag tctataagct ctttatctgt tctctgcccg taggggcctg    3240
ctgggttctc tgtaatacct gtaacgattg gcaatttgtt atatattagt ctaaccataa    3300
aactcttcaa aagtaaccag ttggattaat aaatgattcc agaatgtaaa aaaaaaaaaa    3360
aaaa                                                                  3364
```

PDK INHIBITOR COMPOUNDS AND METHODS OF USE THEREOF

CROSS-REFERENCE TO RELATED APPLICATIONS

This application is the U.S. National Phase Application of PCT/US2009/004949, which, claims the benefit of the following U.S. Provisional Application No.: 61/190,844, which was filed on Sep. 2, 2008; the entire contents of each of these applications is hereby incorporated by reference.

SEQUENCE LISTING

The instant application contains a Sequence Listing which has been submitted in ASCII format via EFS-Web and is hereby incorporated by reference in its entirety. Said ASCII copy, created on Jun. 2, 2011, is named 81827US4.txt and is 10,250 bytes in size.

BACKGROUND OF THE INVENTION

Mitochondrial function is integral to normal homeostasis and cell survival, which are optimally mediated by efficient conversion of substrate fuel into ATP and by precise coordination of nuclear and mitochondrial genomes. Mitochondrial function has been implicated in the etiopathology of such diverse conditions as aging, apoptosis, necrosis and other acquired and congenital diseases. See, e.g., Schon, E. A., *Trends Biochem. Sci.* 25:555-560 (2000); Orth, M. and Schapira, *Am. J. Med. Genet.*, 106:27-36 (2001); Wallace, D. C., *Ment. Retard. Dev. Disabil. Res. Rev.* 7:158-166 (2001).

One determinant of mitochondrial energetics is the activity of pyruvate dehydrogenase complex (PDC), which is entirely nuclear-encoded and comprises three functionally independent enzymes. PDC catalyzes the rate-determining step in aerobic carbohydrate metabolism and mediates conversion of fuel into energy. PDC activity, in turn, is regulated by reversible phosphorylation (inactivation) of its E1 alpha subunit. PDC deficiency is associated with a number of diseases and disorders. Congenital defects in PDC are typically due to mutations in E1α, typified by lactic acidosis, neurodegeneration and early death. Acquired deficiencies in PDC have been associated with other metabolic or neurodegenerative disorders.

PDC is regulated, in part, by reversible phosphorylation wherein the phosphorylated enzyme complex is inactive. Phosphorylation of certain residues is mediated by pyruvate dehydrogenase kinase (PDK). More specifically, phosphorylation of serine residues on the E1α subunit renders the PDC inactive. Thus, compounds that inhibit PDK block the phosphorylation of PDC resulting in greater amounts of the enzyme in its unphosphorylated, active state.

Numerous disorders caused solely or in part by abnormal regulation of PDC in including humans remain unmet with regard to treatment agents and protocols. As such, agents and therapeutic methods capable of stimulating the activity of PDC, including e.g., inhibition of PDK or increasing expression of PDC, are relevant for amelioration of diseases, disorders, or symptoms thereof that are mediated by abnormal PDC regulation.

BRIEF SUMMARY OF THE INVENTION

The compounds and methods herein are useful in treating or preventing acquired or congenital mitochondrial diseases or disorders. The invention relates to a method of treating a subject suffering from or susceptible to a PDC-mediated disorder or disease, the method comprising administering to a subject in need thereof a therapeutically effective amount of a compound that activates PDC activity, to thereby treat the subject suffering from or susceptible to a PDC-mediated disorder or disease. In other aspects, the method is: that wherein the subject is identified as in need of treatment by administration of an PDK2 inhibitor compound; that wherein the subject is identified as in need of treatment by administration of a PDK2 inhibitor compound that is demonstrated to bind to PDK2 at an amino acid sequence comprising PDK2 amino acid residues L53, Y80, S83, I111, R112, R114, H115, R154, I157, R158, I161; that wherein the pyruvate dehydrogenase complex (PDC) is activated via PDK2 inhibition; that wherein the PDK2 inhibitor compound is a compound of Table 1 that was demonstrated to increase pyruvate dehydrogenase complex (PDC) activity in human fibroblast cultures; that further comprising administration to the subject of a nucleic acid that encodes pyruvate dehydrogenase (PDH) E1 alpha; that wherein the nucleic acid is transferred using an adeno-associated virus (AAV) serotype vector; that wherein the AAV serotype vector is AAV serotype 3; or that where the subject is a human.

The invention relates to a method of treating a subject suffering from or susceptible to a cell proliferation related disorder or disease, the method comprising administering to a subject in need thereof a therapeutically effective amount of a pyruvate dehydrogenase kinase 2 (PDK2) protein inhibitor, to thereby treat the subject suffering from or susceptible to a cell proliferation related disorder or disease. In other aspects, the PDK2 inhibitor compound is demonstrated to bind to PDK2 at an amino acid sequence comprising PDK2 amino acid residues L53, Y80, S83, I111, R112, R114, H115, R154, I157, R158, I161.

In aspects, the PDK2 inhibitor inhibits mitochondrial PDK. In other aspects, the PDK2 inhibitor is selected from a compound of Table 1, or a pharmaceutically acceptable salt or prodrug thereof.

Another aspect is a computer for producing a three-dimensional representation of a molecule or molecular complex, wherein said molecule or molecular complex comprises a binding pocket defined by structural coordinates of a binding pocket defined at least in part by structure coordinates of one or more of PDK2 amino acid residues L53, Y80, S83, I111, R112, R114, H115, R154, I157, R158, I161 in, or a homologous binding pocket; or b) a three-dimensional representation of a homologue of said molecule or molecular complex, wherein said homologue comprises a binding pocket that has a root mean square deviation from the backbone atoms of said amino acids of not more than about 2.0 angstroms; the computer comprising:

(i) a machine-readable data storage medium comprising a data storage material encoded with machine-readable data, wherein said data comprises the structural coordinates of a binding pocket defined (at least in part) by structure coordinates of one or more of PDK2 amino acid residues L53, Y80, S83, I111, R112, R114, H115, R154, I157, R158, I161, or a homologous binding pocket;

(ii) a working memory for storing instructions for processing said machine-readable data;

(iii) a central-processing unit coupled to said working memory and to said machine-readable data storage medium for processing said machine readable data into said three-dimensional representation; and (iv) a display coupled to said central-processing unit for displaying said three-dimensional representation.

In other aspects, the binding pocket comprises using the atomic coordinates of an amino acid sequence comprising PDK2 amino acid residues that bind to dichloroacetate (DCA).

Another aspect is a method for identifying a chemotherapeutic agent for the treatment of cancer, the method comprising:

a) obtaining a structural representation of PDK2 or obtaining information relating to the structure of PDK2, and b) modeling a test compound into or on the structure coordinates of the structural representation of PDK2 to determine whether the compound inhibits PDK2;

thereby identifying a chemotherapeutic agent for the treatment of cancer.

Another aspect is a method of identifying a compound useful for inhibiting PDK2 activity comprising the steps of:
1. Obtaining the crystal structure of human PDK2, whereby a three-dimensional structure of PDK2 will be generated;
2. Determination of PDK2 binding regions or pockets by mapping the atomic coordinates of selected amino acid residues, pyruvate dehydrogenase kinase 2, to provide an PDK2 modeling system, then providing a machine readable storage medium which comprises the three-dimensional PDK2 structure and binding pocket(s) defined (at least in part) by structure coordinates of one or more of PDK2 amino acid residues pyruvate dehydrogenase kinase 2;
3. Employing the PDK2 modeling system to identify test compounds that bind within the selected PDK2 binding pockets;
4. Identifying compounds that inhibit PDK2 to the extent of cell growth inhibition or cell death.

Other aspects are a method of treating a subject suffering from or susceptible to a pyruvate dehydrogenase complex (PDC)-mediated disorder or disease, the method comprising administering to a subject in need thereof a therapeutically effective amount of a nucleic acid that encodes pyruvate dehydrogenase (PDH) E1 alpha, to thereby treat the subject suffering from or susceptible to PDC mediated disorder or disease. In other aspects, the method is that wherein the disorder or disease is a cell proliferation related disorder or disease; or that wherein the nucleic acid is transferred using an adeno-associated virus (AAV) serotype vector (e.g., AAV serotype 3).

Other aspects of the invention include pharmaceutical compositions (e.g., formulations) comprising the compounds delineated herein, and methods comprising administration of such compositions.

In yet another aspect, the invention provides the use of a compound of any of the formulae herein alone or together with one or more of the above-described second therapeutic agents in the manufacture of a medicament, either as a single composition or as separate dosage forms, for treatment or prevention in a subject of a disease, disorder or symptom set forth above. Another aspect of the invention is a compound of the formulae herein for use in the treatment or prevention in a subject of a disease, disorder or symptom thereof delineated herein

BRIEF DESCRIPTION OF THE DRAWINGS

The present invention is further described below with reference to the following non-limiting examples and with reference to the following figures, in which:

As shown in FIG. 2, there was no apparent dose-dependent increase in PDH activity with any of the NCI compounds. All compounds increased PDH activity compared to DMSO control (p≦0.05) in one or more concentrations that we used. Compounds 10(Panel A) and 14 (Panel B) were more potent than DCA in increasing PDH activity at 0.01 mM. Similar to $DCA^5$, compound 14 increased PDH activity at 5mM. However, cells treated with 5mM of compounds 10 and 18 caused a significant decrease in PDH activity. PDH activity in fibroblasts treated with varying concentrations of compounds 10 (Panel A), 14 (Panel B), 18 (Panel C), 24 (Panel D), and 25 (Panel E). DMSO and DCA were used as vehicle and positive control, respectively, * ps 0.05 compared to DMSO control: ‡ ps 0.05 compared to DSA.

DETAILED DESCRIPTION OF THE INVENTION

1. Definitions

Figure 1:
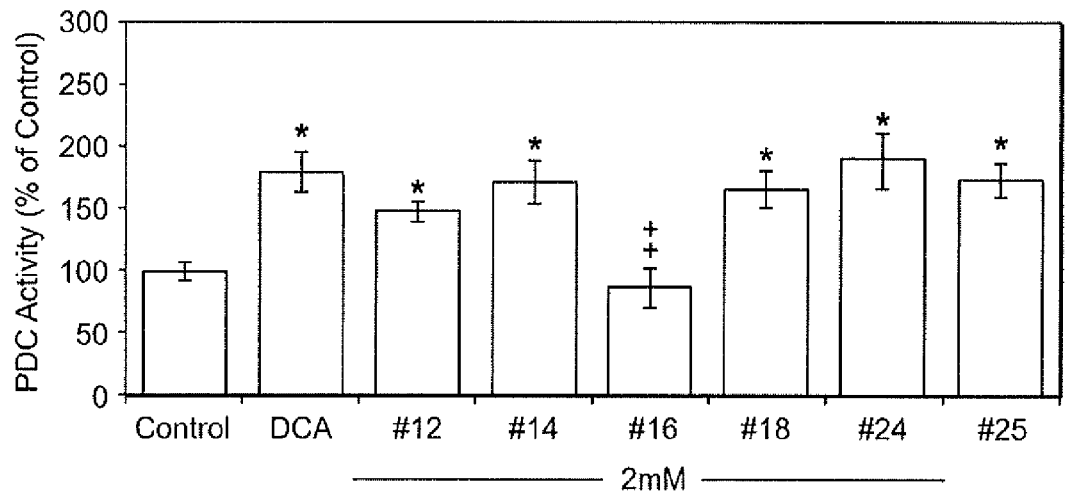
FIG. 1 illustrates PDC activity of various compounds. PDH activity was 180 to 195% higher in cells treated with DCA compared to DMSO control (FIG. 1 Panel A and B). Six of the NCI compounds (compounds 12, 14, 18, 24, and 25 in Panel A and compound 10 in Panel B) also significantly increased PDH activity. NCI compounds 5, 6 and 7 were poorly soluble in DMSO and were tested at a concentration of 0.25 mM. However, none of these compounds stimulated PDH activity (data not shown). PDH activity in fibroblasts treated with DCA or NCI compounds. Data are mean ±SEM of PDH activity in 3 cell lines, * ps 0.05 compared to DMSO control: ‡ ps 0.05 compared to DSA.
Figure 1:
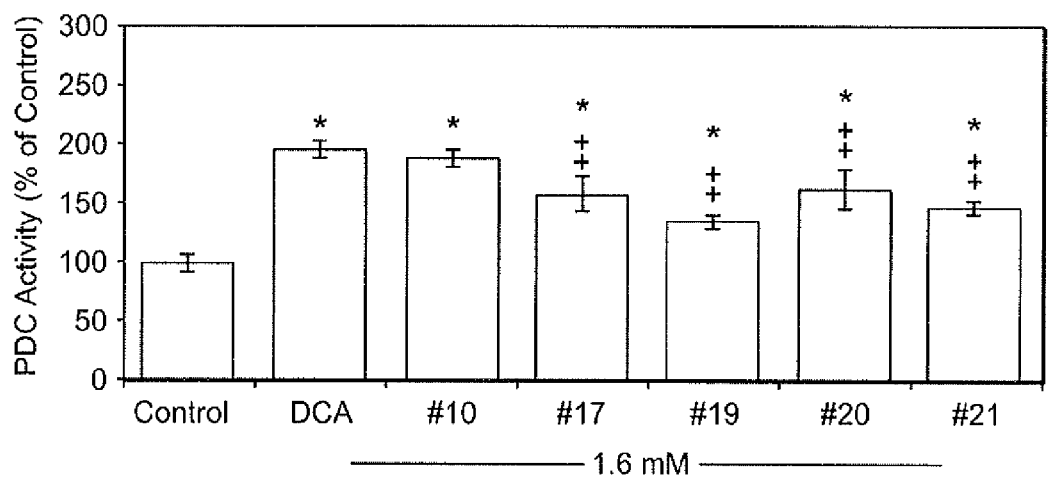
Figure 2:
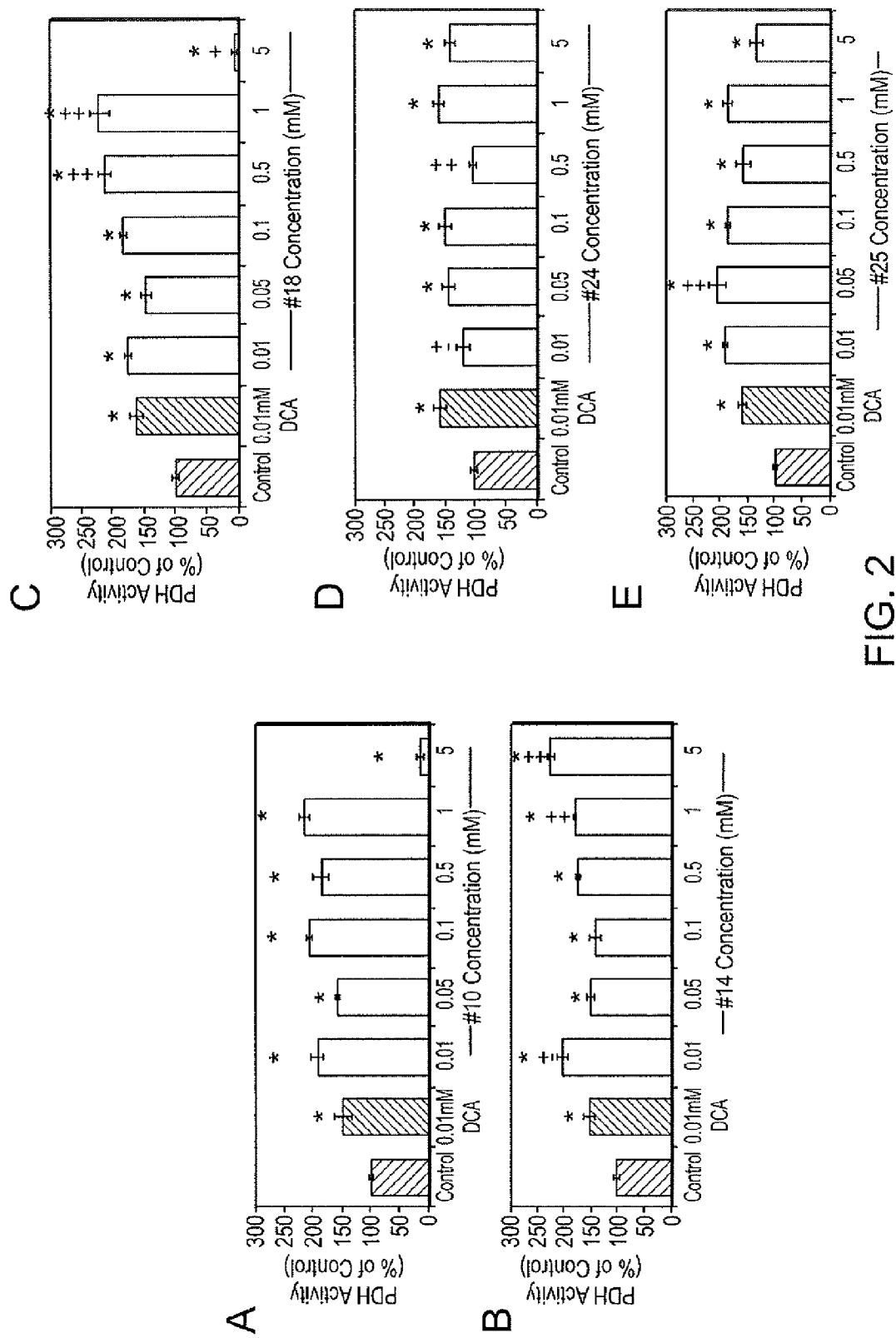
FIG. 2 illustrates PDH activity of various compounds.

Before further description of the present invention, and in order that the invention may be more readily understood, certain terms are first defined and collected here for convenience.

The term "administration" or "administering" includes routes of introducing the compound of the invention(s) to a subject to perform their intended function. Examples of routes of administration that may be used include injection (subcutaneous, intravenous, parenteral, intraperitoneal, intrathecal), oral, inhalation, rectal and transdermal. The pharmaceutical preparations may be given by forms suitable for each administration route. For example, these preparations are administered in tablets or capsule form, by injection, inhalation, eye lotion, ointment, suppository, etc. administration by injection, infusion or inhalation; topical by lotion or ointment; and rectal by suppositories. Oral administration is preferred. The injection can be bolus or can be continuous infusion. Depending on the route of administration, the compound of the invention can be coated with or disposed in a selected material to protect it from natural conditions which may detrimentally affect its ability to perform its intended function. The compound of the invention can be administered alone, or in conjunction with either another agent as described above or with a pharmaceutically-acceptable carrier, or both. The compound of the invention can be administered prior to the administration of the other agent, simultaneously with the agent, or after the administration of the agent. Furthermore, the compound of the invention can also be administered in a proform which is converted into its active metabolite, or more active metabolite in vivo.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone, e.g., oxygen, nitrogen, sulfur or phosphorous atoms. In preferred embodiments, a straight chain or branched chain alkyl has 30 or fewer carbon atoms in its backbone (e.g., $C_1$-$C_{30}$ for straight chain, $C_3$-$C_{30}$ for branched chain), preferably 26 or fewer, and more preferably 20 or fewer, and still more preferably 4 or fewer. Likewise, preferred cycloalkyls have from 3-10 carbon atoms in their ring structure, and more preferably have 3, 4, 5, 6 or 7 carbons in the ring structure.

Moreover, the term alkyl as used throughout the specification and sentences is intended to include both "unsubstituted alkyls" and "substituted alkyls," the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "alkylaryl" moiety is an alkyl substituted with an aryl (e.g., phenylmethyl (benzyl)). The term "alkyl" also includes unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six, and still more preferably from one to four carbon atoms in its backbone structure, which may be straight or branched-chain. Examples of lower alkyl groups include methyl, ethyl, n-propyl, i-propyl, tert-butyl, hexyl, heptyl, octyl and so forth. In preferred embodiment, the term "lower alkyl" includes a straight chain alkyl having 4 or fewer carbon atoms in its backbone, e.g., $C_1$-$C_4$ alkyl.

The terms "alkoxyalkyl," "polyaminoalkyl" and "thioalkoxyalkyl" refer to alkyl groups, as described above, which further include oxygen, nitrogen or sulfur atoms replacing one or more carbons of the hydrocarbon backbone, e.g., oxygen, nitrogen or sulfur atoms.

The terms "alkenyl" and "alkynyl" refer to unsaturated aliphatic groups analogous in length and possible substitution to the alkyls described above, but that contain at least one double or triple bond, respectively. For example, the invention contemplates cyano and propargyl groups.

The term "aryl" as used herein, refers to the radical of aryl groups, including 5- and 6-membered single-ring aromatic groups that may include from zero to four heteroatoms, for example, benzene, pyrrole, furan, thiophene, imidazole, benzoxazole, benzothiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles," "heteroaryls" or "heteroaromatics." The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The language "biological activities" of a compound of the invention includes all activities elicited by compound of the inventions in a responsive cell or subject. It includes genomic and non-genomic activities elicited by these compounds.

"Biological composition" or "biological sample" refers to a composition containing or derived from cells or biopolymers. Cell-containing compositions include, for example, mammalian blood, red cell concentrates, platelet concentrates, leukocyte concentrates, blood cell proteins, blood plasma, platelet-rich plasma, a plasma concentrate, a precipitate from any fractionation of the plasma, a supernatant from any fractionation of the plasma, blood plasma protein fractions, purified or partially purified blood proteins or other components, serum, semen, mammalian colostrum, milk, saliva, placental extracts, a cryoprecipitate, a cryosupernatant, a cell lysate, mammalian cell culture or culture medium, products of fermentation, ascites fluid, proteins induced in blood cells, and products produced in cell culture by normal or transformed cells (e.g., via recombinant DNA or monoclonal antibody technology). Biological compositions can be cell-free. In a preferred embodiment, a suitable biological composition or biological sample is a red blood cell suspension. In some embodiments, the blood cell suspension includes mammalian blood cells. Preferably, the blood cells are obtained from a human, a non-human primate, a dog, a cat, a horse, a cow, a goat, a sheep or a pig. In preferred embodiments, the blood cell suspension includes red blood cells and/or platelets and/or leukocytes and/or bone marrow cells. In some embodiments, the sample includes a marker (e.g., genetic material, mutant form, chemical or biological tag or identifier) suitable for following disorder or disease progression.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "effective amount" includes an amount effective, at dosages and for periods of time necessary, to achieve the desired result, e.g., sufficient to treat a cell proliferation related disorder or disease or an associated condition. An effective amount of compound of the invention may vary according to factors such as the disease state, age, and weight of the subject, and the ability of the compound of the invention to elicit a desired response in the subject. Dosage regimens may be adjusted to provide the optimum therapeutic response. An effective amount is also one in which any toxic or detrimental effects (e.g., side effects) of the compound of the invention are outweighed by the therapeutically beneficial effects.

A therapeutically effective amount of compound of the invention (i.e., an effective dosage) may range from about 0.001 to 30 mg/kg body weight, or from about 0.01 to 10 mg/kg body weight, or from about 0.05 to 5 mg/kg body weight, or from about 0.1 to 1 mg/kg, 0.2 to 0.9 mg/kg, 0.3 to 0.8 mg/kg, 0.4 to 0.7 mg/kg, or 0.5 to 0.6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound of the invention can include a single treatment or, preferably, can include a series of treatments. In one example, a subject is treated with a compound of the invention in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of a compound of the invention used for treatment may increase or decrease over the course of a particular treatment.

The term "enantiomers" refers to two stereoisomers of a compound which are non-superimposable mirror images of one another. An equimolar mixture of two enantiomers is called a "racemic mixture" or a "racemate."

The term "haloalkyl" is intended to include alkyl groups as defined above that are mono-, di- or polysubstituted by halogen, e.g., fluoromethyl and trifluoromethyl.

The term "halogen" designates —F, —Cl, —Br or —I.

The term "hydroxyl" means —OH.

The term "heteroatom" as used herein means an atom of any element other than carbon or hydrogen. Preferred heteroatoms are nitrogen, oxygen, sulfur and phosphorus.

The term "homeostasis" is art-recognized to mean maintenance of static, or constant, conditions in an internal environment.

The language "improved biological properties" refers to any activity inherent in a compound of the invention that enhances its effectiveness in vivo. In a preferred embodiment, this term refers to any qualitative or quantitative improved therapeutic property of a compound of the invention, such as reduced toxicity.

The term "optionally substituted" is intended to encompass groups that are unsubstituted or are substituted by other than hydrogen at one or more available positions, typically 1, 2, 3, 4 or 5 positions, by one or more suitable groups (which may be the same or different). Such optional substituents include, for example, hydroxy, halogen, cyano, nitro, $C_1$-$C_8$alkyl, $C_3$-$C_8$cycloalkyl, $C_2$-$C_8$ alkenyl, $C_2$-$C_8$alkynyl, $C_1$-$C_8$alkoxy, $C_2$-$C_8$alkyl ether, $C_3$-$C_8$alkanone, $C_1$-$C_8$alkylthio, amino, mono- or di-($C_1$-$C_8$alkyl)amino, halo$C_1$-$C_8$alkyl, $C_1$-$C_8$alkoxy, $C_1$-$C_8$alkanoyl, $C_2$-$C_8$alkanoyloxy, $C_1$-$C_8$alkoxycarbonyl, —COON, —CONH2, mono- or di-($C_1$-$C_8$alkyl)aminocarbonyl, —$SO_2NH_2$, and/or mono or di($C_1$-$C_8$alkyl)sulfonamido, as well as carbocyclic and heterocyclic groups. Optional substitution is also indicated by the phrase "substituted with from 0 to X substituents," where X is the maximum number of possible substituents. Certain optionally substituted groups are substituted with from 0 to 2, 3 or 4 independently selected substituents (i.e., are unsubstituted or substituted with up to the recited maximum number of substitutents).

The term "isomers" or "stereoisomers" refers to compounds which have identical chemical constitution, but differ with regard to the arrangement of the atoms or groups in space.

The term "obtaining" as in "obtaining the PDK2 inhibitor compound" is intended to include purchasing, synthesizing or otherwise acquiring the PDK2 inhibitor compound.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The terms "polycyclyl" or "polycyclic radical" refer to the radical of two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The term "prodrug" includes compounds with moieties that can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included.

The language "cell proliferation related disorder or disease" refers to diseases or conditions related to uncontrolled or disregulated cell growth or proliferation. Exemplary cell proliferation related disorders or diseases include, but are not limited to cancer (cancers include cancer of the colon, breast, bone, brain and others (e.g., osteosarcoma, neuroblastoma, colon adenocarcinoma, glioblastoma), cardiac cancer (e.g., sarcoma, myxoma, rhabdomyoma, fibroma, lipoma and teratoma); lung cancer (e.g., bronchogenic carcinoma, alveolar carcinoma, bronchial adenoma, sarcoma, lymphoma, chondromatous hamartoma, mesothelioma); various gastrointestinal cancer (e.g., cancers of esophagus, stomach, pancreas, small bowel, and large bowel); genitourinary tract cancer (e.g., kidney, bladder and urethra, prostate, testis; liver cancer (e.g., hepatoma, cholangiocarcinoma, hepatoblastoma, angiosarcoma, hepatocellular adenoma, hemangioma); bone cancer (e.g., osteogenic sarcoma, fibrosarcoma, malignant fibrous histiocytoma, chondrosarcoma, Ewing's sarcoma, malignant lymphoma, multiple myeloma, malignant giant cell tumor chordoma, osteochronfroma, benign chondroma, chondroblastoma, chondromyxofibroma, osteoid osteoma and giant cell tumors); cancers of the nervous system (e.g., of the skull, meninges, brain, and spinal cord); gynecological cancers (e.g., uterus, cervix, ovaries, vulva, vagina); hematologic cancer (e.g., cancers relating to blood, Hodgkin's disease, non-Hodgkin's lymphoma); skin cancer (e.g., malignant melanoma, basal cell carcinoma, squamous cell carcinoma, Karposi's sarcoma, moles dysplastic nevi, lipoma, angioma, dermatofibroma, keloids, psoriasis); and cancers of the adrenal glands (e.g., neuroblastoma).

As used herein, "obtaining a biological sample from a subject," includes obtaining a sample for use in the methods described herein. A biological sample is described above.

The language "a prophylactically effective amount" of a compound refers to an amount of a compound of the invention of the formula (I), Table 1 compound, or compound otherwise described herein which is effective, upon single or multiple dose administration to the patient, in preventing or treating a cell proliferation related disorder or disease.

The language "reduced toxicity" is intended to include a reduction in any undesired side effect elicited by a compound of the invention when administered in vivo.

The language "selective PDK2 inhibitor" refers to a compound capable of inhibiting the activity of PDK2 while not substantially inhibiting the activity of at least one other kinase enzyme at the same compound concentration. For example, a selective PDK2 inhibitor may have PDK2 inhibitory activity 2, 5, 10, 20, 50, 100, 500, or 1000-fold more potent than against another kinase target inhibitory activity.

The term "sulfhydryl" or "thiol" means —SH.

The term "subject" includes organisms which are capable of suffering from a cell proliferation related disorder or disease or who could otherwise benefit from the administration of a compound of the invention of the invention, such as human and non-human animals. Preferred human animals include human patients suffering from or prone to suffering from a cell proliferative disease or disorder, as described herein. The term "non-human animals" of the invention includes all vertebrates, e.g., mammals, e.g., rodents, e.g., mice, and non-mammals, such as non-human primates, e.g., sheep, dog, cow, chickens, amphibians, reptiles, etc. "Susceptible to a cell proliferative disease or disorder" is meant to include subjects at risk of developing a cell proliferative disease or disorder, including cancer.

The phrases "systemic administration," "administered systemically", "peripheral administration" and "administered peripherally" as used herein mean the administration of a compound of the invention(s), drug or other material, such that it enters the patient's system and, thus, is subject to metabolism and other like processes, for example, subcutaneous administration.

The language "therapeutically effective amount" of a compound of the invention of the invention refers to an amount of an agent which is effective, upon single or multiple dose administration to the patient, in treating or preventing a cell proliferative disease or disorder or an associated condition or symptom, or in prolonging the survivability of the patient with such condition beyond that expected in the absence of such treatment.

By "contacting a cell" is meant providing an agent to a cell in a manner that the agent can have an effect on the cell. For example, in culture, an agent can be added to culture media, with or without the carriers or agents to promote cell entry or uptake (e.g, transfection reagents, liposomes). In an animal, the agent can be administered by any parenteral, enteral, or topical route of administration that allows a The terms "identical" or percent "identity," in the context of two or more nucleic acids or polypeptide sequences, refer to two or more sequences or subsequences that are the same or have a specified percentage of amino acid residues or nucleotides that are the same (e.g., 60% identity, optionally 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Optionally, the identity exists over a region that is at least about 20 amino acids or nucleotides in length, or more preferably over a region that is 25-30 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

Sequence alignments can be used to determine amino acids that are more or less conserved between species. Alteration of non-conserved amino acids typically has less of an effect on the activity of a polypeptide than mutation of a conserved amino acid. Similarly, more conservative mutations, based on charge and/or size of the amino acid, typically have less of an effect on the activity of a polypeptide. For example a conservative mutation would include substitution of one small, neutral, non-polar amino acid such as alanine, glycine, isoleucine, leucine, proline, and valine for another. Similarly, mutation of a glutamic acid to an aspartic acid, or vice versa would also be considered a conservative mutation. Exchange of phenylalanine, tyrosine, and tryptophan for each other would be considered a conservative mutation. Alternatively, alterations in sequence can include substitution of one small, neutral amino acid for another small neutral amino acid, or one small, neutral amino acid for a large neutral amino acid. Protein tolerance to random mutations is understood in the art, for example, see Guo et al. (Protein tolerance to random amino acid change. Proc. Natl. Acad. Sci. USA 101:9205-9210, 2004, incorporated herein by reference).

The phrase "nucleic acid that encodes pyruvate dehydrogenase (PDH) E1 alpha" and the like refer to the coding sequence for at least a fragment of PDH E1 alpha that has at least about 50%, 60%, 70%, 80%, 90%, 95% or more activity (e.g., oxidoreductase activity, acetyl transferase activity) relative to a wild-type sequence when incorporated into a PD complex. Nucleic acids encoding PDH E1 alpha include, but are not limited to mammalian PDH E1 alpha subunits, for example from mouse (Accession No. NM_008811.1 (SEQ ID NO: 1)), rat (Accession No. NM_053994.2 (SEQ ID NO: 2)), human (Accession No. NM_000284.2(SEQ ID NO: 3)). Each of the Accession Nos. is incorporated herein by reference in the version available on the date of filing of the instant application. It is understood that alterations of the nucleic acid sequence to include modifications that do not alter the coding sequence of the protein are included within the phrase of nucleic acids that encode PDH E1 alpha. Nucleic acid that encodes PDH E1 alpha is understood as a nucleic acid that encodes a protein that is at least about 70%, 80%, 90%, 95% identical to a wild-type sequence that has at least about 50%, 60%, 70%, 80%, 90%, 95% or more activity (e.g., oxidoreductase activity, acetyl transferase activity) relative to a wild-type sequence when incorporated into a PD complex.

The phrase "operably linked to a promoter sequence" is understood as a coding sequence for an amino acid or polypeptide is juxtaposed to a promoter sequence, so that the nucleic acid sequence will be expressed in a cell. The selection of a promoter sequence is routine in the art. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

The phrase "expression vector" is understood as a nucleic acid that encodes the polypeptide to be expressed operably linked to a promoter and preferably further including sequences that allow for replication of the vector. The expression vector can be "naked", i.e., not encapsulated in a virus or other particle. Encapsulated in an artificial or synthetic particle (lipoplex, polyplex, or dendrimer). The expression vector can be a viral vector appropriate for administration to mammals, particularly human mammals. For example the viral vector can be a retroviral vector, adenoviral vector, adeno-associated viral vector (AAV), or herpesvirus viral vector. Viral vectors are available in many serotypes with various tropisms. Such properties are well known to those of skill in the art. Methods of construction of expression vectors and viral vectors is well known in the art.

The expression vector material is generally produced by culture of recombinant or transfected cells and formulated in a pharmacologically acceptable solution or suspension, which is usually a physiologically-compatible aqueous solution, or in coated tablets, tablets, capsules, suppositories, inhalation aerosols, or ampules, as described in the art, for example in U.S. Pat. No. 4,446,128, incorporated herein by reference.

The vector-containing composition is administered to a mammal exhibiting abnormal glucose or insulin sensitivity, secretion, or signaling in an amount sufficient to transfect a substantial portion of the target cells of the mammal. Administration may be any suitable route, including oral, rectal, inhalation, intranasal or by intravesicular (e.g., bladder) instillation or injection where injection may be, for example, transdermal, subcutaneous, intramuscular in intravenous. Preferably, the expression vector is administered to the mammal so that the target cells of the mammal are preferentially transfected. Determination of the amount to be administered will involve consideration of infectivity of the vector, transfection efficiency in vitro, immune response of the patient, etc. A typical initial dose for administration would be 10-1000 micrograms when administered intravenously, intramuscularly, subcutaneously, intravesicularly, or in inhalation aerosol, 100 to 1000 micrograms by mouth, 105 to 1010 plaque forming units of a recombinant vector, although this amount may be adjusted by a clinician doing the administration as commonly occurs in the administration of other pharmacological agents. A single administration may usually be sufficient to produce a therapeutic effect, but multiple administrations may be necessary to assure continued response over a substantial period of time.

As used herein, "isolated" or "purified" is understood as being removed from its usual environment or other components with which they are naturally associated. For example, an isolated cell can be removed from an animal and placed in a culture dish or another animal. Isolated is not meant as being removed from all other cells. A polypeptide or nucleic acid is isolated when it is about 80% free, 85% free, 90% free, 95% free from other cellular material typically associated with the nucleic acid or polypeptide (e.g., material in a cell in which the nucleic acid or peptide is endogenously expressed), or substantially free of chemical precursors or other chemicals when chemically synthesized. An "isolated polypeptide" or "isolated polynucleotide" is, therefore, a substantially purified polypeptide or polynucleotide, respectively. As used herein "homogeneously purified" is understood as at least about 90%, 95%, 98%, or 99% free from other biological materials or synthesis reagents used in the preparation of the polypeptide or nucleic acid. A homogeneously purified polypeptide or nucleic acid may be in a composition in a pharmaceutically acceptable carrier and/or buffer solution (e.g., for storage).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res., 19:5081 (1991); Ohtsuka et al., J. Biol. Chem. 260: 2605-2608 (1985); Rossolini et al., Mol. Cell Probes, 8:91-98 (1994)). The term nucleic acid is used interchangeably with gene, cDNA, mRNA, oligonucleotide, and polynucleotide.

As used herein, the term "recombinant DNA molecule" as used herein refers to a DNA molecule, which is comprised of segments of DNA joined together by means of molecular biological techniques.

The term "reporter gene" which is typically used in the context of a "reporter construct" is understood as a coding sequence for a polypeptide that is operably linked to a promoter sequence. The coding sequence for a polypeptide encodes a polypeptide that can be readily detected, preferably in a quantitative manner, such as alkaline phosphatase, beta-galactosidase, luciferase, green fluorescent protein, etc. Methods to detect the presence of such proteins is well known in the art and can be performed using any of a number of commercially available kits and automated readers. The selection of a reporter gene is a matter of choice.

As used herein, a "normal cell" is a cell that is derived from tissue that does not include any known mutations or disruptions that predispose the cell to disease or dysfunction.

With respect to the nomenclature of a chiral center, terms "d" and "l" configuration are as defined by the IUPAC Recommendations. As to the use of the terms, diastereomer, racemate, epimer and enantiomer will be used in their normal context to describe the stereochemistry of preparations.

2. Compounds of the Invention

In one aspect, the invention provides a compound capable of inhibiting PDK activity (e.g., PDK1, PDK2, PDK3 or PDK4). In one aspect, the invention provides a compound capable of inhibiting PDK2 activity. In certain embodiments, the compound is capable of inhibiting PDK2 activity selectively, e.g., without concomitant inhibition of other kinases.). In one aspect, the invention provides a compound identified as an inhibitor of PDK2 activity.

In certain embodiments, the PDK2 inhibitor compound is any compound (or salt, solvate or prodrug thereof) of Table 1:

TABLE 1

| Cmpd No. | NCS ID No. | Name |
|---|---|---|
| 5 | 19191 | 2-sulfoacetic acid |
| 6 | 282047 | 2-(2H-tetrazol-5-yl)acetic acid |
| 7 | 60519 | 2-oxopropanedioic acid |
| 10 | 65438 | 2-methylbut-2-enedioic acid |
| 12 | 69870 | 2,3-dihydroxybutanoic acid |
| 14 | 60104 | 2-(3H-imidazol-4-yl)acetic acid |
| 16 | 112245 | oxalic acid |
| 17 | 295473 | 2-(carbamoylamino)-2-methoxyacetic acid |
| 18 | 89558 | (E)-3-chlorobut-2-enoic acid |
| 19 | 521674 | thiadiazole-4-carboxylic acid |
| 20 | 56801 | 4-amino-6-oxo-3H-pyrimidine-2-carboxylic acid |
| 21 | 179393 | (Z)-3-bromoprop-2-enoic acid |
| 22 | 9924 | 2-hydrazinyl-2-oxoacetic acid |
| 24 | 206946 | (Z)-but-2-enoic acid |
| 25 | 15826 | 2-formamidoacetic acid |
| 26 | | tartaric acid | or a pharmaceutically acceptable salt or prodrug thereof.

In general, a compound of the invention will be selected such that the compound is capable of binding to a binding site or pocket of PDK2 that is defined (at least in part) by structure coordinates of one or more of PDK2 amino acid residues (L53, Y80, S83, I111, R112, R114, H115, R154, I157, R158, I161). Moreover, in certain embodiments, a compound has one or more of the following properties: (1) not more than 5 hydrogen bond donors; (2) not more than 10 hydrogen bond acceptors; (3) a molecular weight of 1000 or less, 800 or less, 600 or less, 500 or less; and (4) a partition coefficient log P of less than 5.

Compounds according to the invention can generally be made according to techniques known in the field (see, e.g., *Comprehensive Organic Synthesis*, Trost, B. M. and Fleming, I. eds., Pergamon Press, Oxford; and references cited therein). Furthermore, compounds of the invention can be purified, separated, or isolated, e.g., by crystallization, chromatographic separation (e.g., by liquid chromatography), or by other methods known in the art.

Naturally occurring or synthetic isomers can be separated in several ways known in the art. Methods for separating a racemic mixture of two enantiomers include chromatography using a chiral stationary phase (see, e.g., "Chiral Liquid Chromatography," W. J. Lough, Ed. Chapman and Hall, New York (1989)). Enantiomers can also be separated by classical resolution techniques. For example, formation of diastereomeric salts and fractional crystallization can be used to separate enantiomers. For the separation of enantiomers of carboxylic acids, the diastereomeric salts can be formed by addition of enantiomerically pure chiral bases such as brucine, quinine, ephedrine, strychnine, and the like. Alternatively, diastereomeric esters can be formed with enantiomerically pure chiral alcohols such as menthol, followed by separation of the diastereomeric esters and hydrolysis to yield the free, enantiomerically enriched carboxylic acid. For separation of the optical isomers of amino compounds, addition of chiral carboxylic or sulfonic acids, such as camphorsulfonic acid, tartaric acid, mandelic acid, or lactic acid can result in formation of the diastereomeric salts.

3. Uses of the Compounds of the Invention

The compounds and methods herein are useful in treating or preventing acquired or congenital mitochondrial diseases or disorders. As described herein below, it has now been found that the compounds of the invention and analogs can be useful to treat or prevent cell proliferative diseases and disorders, including cancer. In another aspect, the compounds delineated herein can be useful to treat or prevent metabolic diseases and disorders, including diabetes, or related conditions associated with insulin resistance, or cardiovascular or central nervous system hypoxic, ischemic or degenerative diseases. In another aspect, the compounds delineated herein can be useful to treat or prevent primary pulmonary hypertension or related conditions that lead to the stimulation of host vascular or endothelial cell growth as a response to diminished oxygen availability, as in hypoxia. In another aspect, the compounds delineated herein can be useful to treat or prevent autoimmune diseases including type I diabetes, rheumatoid arthritis and systemic lupus erythematosus.

Thus, in one aspect, the invention provides a method of treating a subject suffering from or susceptible to a cell proliferation related disorder or disease, the method comprising administering to a subject in need thereof a therapeutically effective amount of a pyruvate dehydrogenase kinase 2 (PDK2) inhibitor, to thereby treat the subject suffering from or susceptible to a cell proliferation related disorder or disease. The PDK2 inhibitor acts to impair growth and/or induce death of abnormal cells.

Thus, in one aspect, the invention provides a method of treating a subject suffering from or susceptible to a metabolic disorder or disease, the method comprising administering to a subject in need thereof a therapeutically effective amount of a pyruvate dehydrogenase kinase 2 (PDK2) inhibitor, to thereby treat the subject suffering from or susceptible to a metabolic disorder or disease.

In one embodiment, the compound is capable of binding to or interacting with a binding site or pocket defined (at least in part) by structure coordinates of one or more PDK2 amino acid residues selected from L53, Y80, S83, I111, R112, R114, H115, R154, I157, R158, I161. In certain embodiments, the compound is a compound disclosed herein, e.g., a compound of Table 1. In certain embodiments, the subject is a mammal, e.g., a primate, e.g., a human.

In another aspect, the invention provides a method of treating a subject suffering from or susceptible to a cell proliferation related disorder or disease, the method comprising inhibiting the activity of pyruvate dehydrogenase kinase 2 (PDK2) in the subject such that the subject is treated.

In one aspect, the invention provides a method of inhibiting the growth of a cell, the method comprising inhibiting the activity of pyruvate dehydrogenase kinase 2 (PDK2) in the cell such that growth of the cell is inhibited. In one embodiment, the compound is capable of binding to or interacting with a binding site or pocket defined (at least in part) by structure coordinates of one or more PDK2 amino acid residues L53, Y80, S83, I111, R112, R114, H115, R154, I157, R158, I161. In certain embodiments, the compound is a compound disclosed herein, e.g., a compound of Table 1.

In one aspect, the invention provides a method of killing a cell, the method comprising inhibiting the activity of pyruvate dehydrogenase kinase 2 (PDK2) in the cell such that the cell is killed.

In another aspect, the invention provides a method for inhibiting activity or expression of PDK2 (e.g., in vitro, in vivo) in a cell or a subject, the method comprising contacting the cell or subject with an effective amount of a compound capable of inhibiting activity of PDK2, such that activity of PDK2 is inhibited.

In another aspect, the invention provides a method for activating pyruvate dehydrogenase complex (PDC) activity (e.g., in vitro, in vivo) in a cell or a subject, the method comprising contacting the cell or subject with an effective amount of a pro-apoptotic gene (e.g., nucleic acid, pyruvate dehydrogenase E1 alpha, parvovirus B19 non-structural (NS1) gene, just another zinc-finger (JAZ) gene) capable of inhibiting activity of PDK2, such that activity of PDK2 is inhibited. In one aspect, the pro-apoptotic gene is delivered using an AAV-mediated gene transfer process, e.g., use of an AAV serotype, particularly AAV serotype 3.

In another aspect, the invention provides a method for activating pyruvate dehydrogenase complex (PDC) activity (e.g., in vitro, in vivo) in a cell or a subject, the method comprising contacting the cell or subject with an effective amount of a compound capable of inhibiting activity of PDK2, such that activity of PDK2 is inhibited.

In another aspect, the invention provides a method for activating pyruvate dehydrogenase complex (PDC) activity (e.g., in vitro, in vivo) in a cell or a subject, the method comprising contacting (e.g., administering to) the cell or subject with an effective amount of a compound (e.g., a compound delineated herein) capable of increasing levels of active PDC (e.g., by increasing expression of E1α, stabilizing levels of E1α that are inactivated, or stabilizing levels of E1α that are phosphorylated), such that activity of PDC is increased relative to that where compound is not administered.

In another aspect, the invention provides a method for activating pyruvate dehydrogenase complex (PDC) activity (e.g., in vitro, in vivo) in a cell or a subject, the method comprising contacting the cell or subject with an effective amount of a pro-apoptotic gene (e.g., nucleic acid, pyruvate dehydrogenase E1 alpha, parvovirus B19 non-structural (NS1) gene, just another zinc-finger (JAZ) gene) capable of inhibiting activity of PDK2, and an effective amount of a compound capable of inhibiting activity of PDK2, such that activity of PDK2 is inhibited.

The present methods can be performed on cells in culture, e.g. in vitro or ex vivo, or on cells present in an animal subject, e.g., in vivo. Compounds of the inventions can be initially tested in vitro using primary cultures of cells.

The present methods can be performed on cells in culture, e.g. in vitro or ex vivo, or on cells present in an animal subject, e.g., in vivo. Compound of the invention can be initially tested in vitro using cells from the respiratory tract from embryonic rodent pups (See e.g. U.S. Pat. No. 5,179,109-fetal rat tissue culture), or other mammalian (See e.g. U.S. Pat. No. 5,089,517-fetal mouse tissue culture) or non-mammalian animal models.

Alternatively, the effects of a compound of the invention can be characterized in vivo using animals models. In certain embodiments, the methods of the invention include administering to a subject a therapeutically effective amount of a compound of the invention in combination with another pharmaceutically active compound. In a further embodiment, the additional therapeutic agent is an anti-cancer agent, chemotherapeutic agent, an anti-angiogenesis agent, cytotoxic agent, or an anti-proliferation agent. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, mercaptopurine, 6-thioguanine, cytarabine (CA), 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, vincristine, vinblastine, etoposide, trimetrexate, teniposide, cisplatin and diethylstilbestrol (DES). See, generally, The Merck Manual of Diagnosis and Therapy, 15th Ed., pp. 1206-1228, Berkow et al., eds., Rahway, N.J., 1987). The compound of the invention and the pharmaceutically active compound may be administered to the subject in the same pharmaceutical composition or in different pharmaceutical compositions (at the same time or at different times).

In another aspect, the invention provides use of an effective amount of a pro-apoptotic gene (e.g., nucleic acid, pyruvate dehydrogenase E1 alpha) capable of inhibiting activity of PDK2, and an effective amount of a compound capable of inhibiting activity of PDK2.

In another aspect, the invention provides a method of treating a subject suffering from or susceptible to a PDC-mediated disorder or disease, wherein the subject has been identified as in need of treatment for a PDC-mediated disorder or disease, comprising administering to said subject in need thereof, an effective amount of a compound or pharmaceutical composition herein, such that said subject is treated for said disorder.

Determination of a therapeutically effective amount or a prophylactically effective amount of the compound of the invention, can be readily made by the physician or veterinarian (the "attending clinician"), as one skilled in the art, by the use of known techniques and by observing results obtained under analogous circumstances. The dosages may be varied depending upon the requirements of the patient in the judgment of the attending clinician; the severity of the condition being treated and the particular compound being employed.

In determining the therapeutically effective amount or dose, and the prophylactically effective amount or dose, a number of factors are considered by the attending clinician, including, but not limited to: the specific cell proliferative disease or disorder involved; pharmacodynamic characteristics of the particular agent and its mode and route of administration; the desired time course of treatment; the species of mammal; its size, age, and general health; the degree of or involvement or the severity of the disease; the response of the individual patient; the particular compound administered; the mode of administration; the bioavailability characteristics of the preparation administered; the dose regimen selected; the kind of concurrent treatment (i.e., the interaction of the compound of the invention with other co-administered therapeutics); and other relevant circumstances.

Treatment can be initiated with smaller dosages, which are less than the optimum dose of the compound. Thereafter, the dosage may be increased by small increments until the optimum effect under the circumstances is reached. For convenience, the total daily dosage may be divided and administered in portions during the day if desired. A therapeutically effective amount and a prophylactically effective amount of a compound of the invention of the invention is expected to vary from about 0.1 milligram per kilogram of body weight per day (mg/kg/day) to about 100 mg/kg/day.

Compounds determined to be effective for the prevention or treatment of cell proliferative diseases or disorders in animals, e.g., dogs, chickens, and rodents, may also be useful in treatment of similar conditions in humans. Those skilled in the art of treatment in humans will know, based upon the data obtained in animal studies, the dosage and route of administration of the compound to humans. In general, the dosage and route of administration in humans is expected to be similar to that in animals.

The identification of those patients who are in need of prophylactic treatment for cell proliferative diseases or disorders is well within the ability and knowledge of one skilled in the art. Certain of the methods for identification of patients which are at risk of developing cell proliferative diseases or disorders which can be treated by the subject methods are appreciated in the medical arts, such as family history, the presence of other risk factors associated with the development of that disease state in the subject patient, and the like. A clinician skilled in the art can readily identify such candidate patients, by the use of, for example, clinical tests, physical examination and medical/family/travel history.

A method of assessing the efficacy of a disease treatment in a subject includes determining the physical condition of the subject (e.g., blood pressure, degree or extent of disorder progression, obtaining a biological sample, and the like) and then administering a therapeutically effective amount of an PDK2 inhibitor compound of the invention to the subject. After a appropriate period of time after the administration of the compound, e.g., 2 hours, 4 hours, 8 hours, 12 hours, or 72 hours, or one week, the physical condition of the subject is determined again. The modulation of the cell proliferative disease or disorder indicates efficacy of an treatment. The physical condition of the subject may be determined periodically throughout treatment. For example, the physical condition of the subject may be checked every few hours, days or weeks to assess the further efficacy of the treatment. The method described may be used to screen or select patients that may benefit from treatment with a PDK2 inhibitor.

In another aspect, the invention provides a method for identifying a compound that modulates (e.g., inhibits) the activity of PDK2, the method comprising using the atomic coordinates of one or more of PDK2 amino acid residues L53, Y80, S83, I111, R112, R114, H115, R154, I157, R158, I161 to generate a three-dimensional structure of a molecule comprising an PDK2 binding pocket, and employing the three-dimensional structure to identify a compound that modulates the activity of PDK2.

In another aspect, a compound of the invention is packaged in a therapeutically effective amount with a pharmaceutically acceptable carrier or diluent. The composition may be formulated for treating a subject suffering from or susceptible to a cell proliferation related disorder or disease, and packaged with instructions to treat a subject suffering from or susceptible to such a disease or condition (e.g., a kit). In aspects, the method of packaging comprises combining the compound or compositions delineated herein in a pharmaceutically acceptable packaging material, In other aspects the method of packaging comprises inserting, printing or attaching instructions (e.g., insert, printing on package, label) in or on the packaging.

In another aspect, the invention provides a packaged composition including a therapeutically effective amount of an PDK2 inhibitor compound and a pharmaceutically acceptable carrier or diluent. The composition may be formulated for treating a subject suffering from or susceptible to a cell proliferation related disorder or disease, and packaged with instructions to treat a subject suffering from or susceptible to a cell proliferation related disorder or disease.

In one aspect, the invention provides a kit for treating a cell proliferation related disorder or disease in a subject is provided and includes a compound disclosed herein, e.g., a compound of Table 1, or a pharmaceutically acceptable ester, salt, and prodrug thereof, and instructions for use. In further aspects, the invention provides kits for treating a cell proliferation related disorder or disease, assessing the efficacy of an anti-cell-proliferative treatment in a subject using an PDK2 inhibitor, monitoring the progress of a subject being treated with an PDK2 inhibitor, selecting a subject with or susceptible to a cell proliferation related disorder or disease, and/or treating a subject suffering from or susceptible to a cell proliferation related disorder or disease. In certain embodiments, the invention provides: a kit for treating a cell proliferation related disorder or disease in a subject, the kit comprising a compound capable of inhibiting activity (or expression) of PDK2, or pharmaceutically acceptable esters, salts, and prodrugs thereof, and instructions for use; in certain embodiments, the compound is represented any of the structures of Table 1, or a pharmaceutically acceptable salt thereof.

In another aspect, the invention provides the use of a compound of the invention for the manufacture of a medicament for the treatment of a cell proliferation related disorder or disease. Another aspect is a compound of the invention for use in treatment or prevention of a disease, disorder or symptom thereof, including those delineated herein.

4. Pharmaceutical Compositions

The invention also provides a pharmaceutical composition, comprising an effective amount of a compound of the invention, e.g., a compound of Table 1, or otherwise described herein and a pharmaceutically acceptable carrier. In a further embodiment, the effective amount is effective to treat a cell proliferation related disorder or disease, as described previously.

In an embodiment, the compound of the invention is administered to the subject using a pharmaceutically-acceptable formulation, e.g., a pharmaceutically-acceptable formulation that provides sustained delivery of the compound of the invention to a subject for at least 12 hours, 24 hours, 36 hours, 48 hours, one week, two weeks, three weeks, or four weeks after the pharmaceutically-acceptable formulation is administered to the subject.

In certain embodiments, these pharmaceutical compositions are suitable for topical or oral administration to a subject. In other embodiments, as described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "pharmaceutically acceptable" refers to those compounds of the present invention, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" includes pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier is "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions containing a compound of the invention(s) include those suitable for oral, nasal, topical (including buccal and sublingual), rectal, vaginal, aerosol and/or parenteral administration. The compositions may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, more preferably from about 10 percent to about 30 percent.

Methods of preparing these compositions include the step of bringing into association a compound of the invention(s) with the carrier and, optionally, one or more accessory ingredients. In general, the formulations are prepared by uniformly and intimately bringing into association a compound of the invention with liquid carriers, or finely divided solid carriers, or both, and then, if necessary, shaping the product.

Compositions of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the invention(s) as an active ingredient. A compound may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compound of the invention(s) include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

In addition to inert diluents, the oral compositions can include adjuvants such as wetting agents, emulsifying and suspending agents, sweetening, flavoring, coloring, perfuming and preservative agents.

Suspensions, in addition to the active compound of the invention(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of the invention for rectal or vaginal administration may be presented as a suppository, which may be prepared by mixing one or more compound of the invention(s) with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Compositions of the present invention which are suitable for vaginal administration also include pessaries, tampons, creams, gels, pastes, foams or spray formulations containing such carriers as are known in the art to be appropriate.

Dosage forms for the topical or transdermal administration of a compound of the invention(s) include powders, sprays, ointments, pastes, creams, lotions, gels, solutions, patches and inhalants. The active compound of the invention(s) may be mixed under sterile conditions with a pharmaceutically-acceptable carrier, and with any preservatives, buffers, or propellants which may be required.

The ointments, pastes, creams and gels may contain, in addition to compound of the invention(s) of the present invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of the invention(s), excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The compound of the invention(s) can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically-acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a compound of the invention(s) to the body. Such dosage forms can be made by dissolving or dispersing the agent in the proper medium. Absorption enhancers can also be used to increase the flux of the active ingredient across the skin. The rate of such flux can be controlled by either providing a rate controlling membrane or dispersing the active ingredient in a polymer matrix or gel.

Ophthalmic formulations, eye ointments, powders, solutions and the like, are also contemplated as being within the scope of the invention.

Pharmaceutical compositions of the invention suitable for parenteral administration comprise one or more compound of the invention(s) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of compound of the invention(s) in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the compound of the invention(s) are administered as pharmaceuticals, to humans and animals, they can be given per se or as a pharmaceutical composition containing, for example, 0.1 to 99.5% (more preferably, 0.5 to 90%) of active ingredient in combination with a pharmaceutically-acceptable carrier.

Regardless of the route of administration selected, the compound of the invention(s), which may be used in a suitable hydrated form, and/or the pharmaceutical compositions of the present invention, are formulated into pharmaceutically-acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular patient, composition, and mode of administration, without being toxic to the patient. An exemplary dose range is from 0.01 to 10 mg per day.

A preferred dose of the compound of the invention for the present invention is the maximum that a patient can tolerate and not develop serious or unacceptable side effects. In certain embodiments, the compound of the present invention is administered at a concentration of about 10 micrograms to about 100 mg per kilogram of body weight per day, about 0.1-about 10 mg/kg or about 1.0 mg-about 10 mg/kg of body weight per day. Ranges intermediate to the above-recited values are also intended to be part of the invention.

5. Screening Methods and Systems

In another aspect, the invention provides a method for identifying a compound that inhibits PDK2 activity, the method comprising obtaining a structure of PDK2 or obtaining information relating to the structure of PDK2, and modeling a test compound into or on the crystal structure coordinates to determine whether the compound inhibits PDK2. In certain embodiments, the step of modeling comprises modeling or determining the ability of the compound to bind to or associate with a binding pocket defined by structure coordinates of one or more PDK2 amino acid residues L53, Y80, S83, I111, R112, R114, H115, R154, I157, R158, I161.

Yet another aspect of the invention is a method for identifying a compound that modulates the activity of PDK2, the method comprising using the atomic coordinates of one or more PDK2 amino acid residues L53, Y80, S83, I111, R112, R114, H115, R154, I157, R158, I161 to generate a three-dimensional structure of a molecule comprising an PDK2 binding site or binding pocket, and employing the three-dimensional structure to identify a compound that modulates (e.g., inhibits) the activity of PDK2.

In another aspect, the invention relates to a three-dimensional structure of PDK2. The invention provides key structural features of PDK2 binding pockets. Another aspect is a structure of PDK2 having the structural coordinates comprising one or more of PDK2 amino acid residues L53, Y80, S83, I111, R112, R114, H115, R154, I157, R158, I161, or a homologous binding pocket. Another aspect is a structure of PDK2 having the structural coordinates comprising one or more of PDK2 amino acid residues that bind to DCA.

In another aspect, the invention provides a machine readable storage medium which comprises the structural coordinates of either one or both of the binding pockets identified herein, or similarly shaped, homologous binding pockets. Such storage media encoded with these data are capable of displaying a three-dimensional graphical representation of a molecule or molecular complex which comprises such binding pockets on a computer screen or similar viewing device. Thus, in one embodiment, the invention provides a machine readable storage medium which comprises the structural coordinates of a binding pocket defined (at least in part) by structure coordinates of one or more of PDK2 amino acid residues L53, Y80, S83, I111, R112, R114, H115, R154, I157, R158, I1161, or a homologous binding site or binding pocket.

In another aspect, the invention provides a computer for producing a three-dimensional representation of a molecule or molecular complex, wherein said molecule or molecular complex comprises a binding pocket defined by structural coordinates of a binding pocket defined (at least in part) by structure coordinates of one or more of PDK2 amino acid residues L53, Y80, S83, I111, R112, R114, H115, R154, I157, R158, I161, or a homologous binding site or pocket; or b) a three-dimensional representation of a homologue of said molecule or molecular complex, wherein said homologue comprises a binding pocket that has a root mean square deviation from the backbone atoms of said amino acids of not more than about 2.0 angstroms. The computer includes (i) a machine-readable data storage medium comprising a data storage material encoded with machine-readable data, wherein said data comprises the structural coordinates of a binding pocket defined (at least in part) by structure coordinates of one or more of PDK2 amino acid residues L53, Y80, S83, I111, R112, R114, H115, R154, I157, R158, I161, or a homologous binding site pocket; (ii) a working memory for storing instructions for processing said machine-readable data; (iii) a central-processing unit coupled to said working memory and to said machine-readable data storage medium for processing said machine readable data into said three-dimensional representation; and (iv) a display coupled to said central-processing unit for displaying said three-dimensional representation.

Thus, the computer produces a three-dimensional graphical structure of a molecule or a molecular complex which comprises a binding site or pocket.

In another embodiment, the invention provides a computer for producing a three-dimensional representation of a molecule or molecular complex defined by structure coordinates of all or some of the PDK2 amino acids, or a three-dimensional representation of a homologue of said molecule or molecular complex, wherein said homologue comprises a binding pocket that has a root mean square deviation from the backbone atoms of said amino acids of not more than 2.0 (more preferably not more than 1.5) angstroms In exemplary embodiments, the computer or computer system can include components which are conventional in the art, e.g., as disclosed in U.S. Pat. No. 5,978,740 and/or 6,183,121 (incorporated herein by reference). For example, a computer system can includes a computer comprising a central processing unit ("CPU"), a working memory (which may be, e.g., RAM (random-access memory) or "core" memory), a mass storage memory (such as one or more disk drives or CD-ROM drives), one or more cathode-ray tube (CRT) or liquid crystal display (LCD) display terminals, one or more keyboards, one or more input lines, and one or more output lines, all of which are interconnected by a conventional system bus.

Machine-readable data of this invention may be inputted to the computer via the use of a modem or modems connected by a data line. Alternatively or additionally, the input hardware may include CD-ROM drives, disk drives or flash memory. In conjunction with a display terminal, a keyboard may also be used as an input device.

Output hardware coupled to the computer by output lines may similarly be implemented by conventional devices. By way of example, output hardware may include a CRT or LCD display terminal for displaying a graphical representation of a binding pocket of this invention using a program such as QUANTA or PYMOL. Output hardware might also include a printer, or a disk drive to store system output for later use.

In operation, the CPU coordinates the use of the various input and output devices, coordinates data accesses from the mass storage and accesses to and from working memory, and determines the sequence of data processing steps. A number of programs may be used to process the machine-readable data of this invention, including commercially-available software.

A magnetic storage medium for storing machine-readable data according to the invention can be conventional. A magnetic data storage medium can be encoded with a machine-readable data that can be carried out by a system such as the computer system described above. The medium can be a conventional floppy diskette or hard disk, having a suitable substrate which may be conventional, and a suitable coating, which may also be conventional, on one or both sides, containing magnetic domains whose polarity or orientation can be altered magnetically. The medium may also have an opening for receiving the spindle of a disk drive or other data storage device.

The magnetic domains of the medium are polarized or oriented so as to encode in manner which may be conventional, machine readable data such as that described herein, for execution by a system such as the computer system described herein.

An optically-readable data storage medium also can be encoded with machine-readable data, or a set of instructions, which can be carried out by a computer system. The medium can be a conventional compact disk read only memory (CD-ROM) or a rewritable medium such as a magneto-optical disk which is optically readable and magneto-optically writable.

In the case of CD-ROM, as is well known, a disk coating is reflective and is impressed with a plurality of pits to encode the machine-readable data. The arrangement of pits is read by reflecting laser light off the surface of the coating. A protective coating, which preferably is substantially transparent, is provided on top of the reflective coating.

In the case of a magneto-optical disk, as is well known, a data-recording coating has no pits, but has a plurality of magnetic domains whose polarity or orientation can be changed magnetically when heated above a certain temperature, as by a laser. The orientation of the domains can be read by measuring the polarization of laser light reflected from the coating. The arrangement of the domains encodes the data as described above.

Structure data, when used in conjunction with a computer programmed with software to translate those coordinates into the 3-dimensional structure of a molecule or molecular complex comprising a binding pocket, may be used for a variety of purposes, such as drug discovery.

For example, the structure encoded by the data may be computationally evaluated for its ability to associate with chemical entities. Chemical entities that associate with a binding site or pocket of PDK2 as disclosed herein may inhibit PDK2 activity, and are potential drug candidates. Alternatively, the structure encoded by the data may be displayed in a graphical three-dimensional representation on a computer screen. This allows visual inspection of the structure, as well as visual inspection of the structure's association with chemical entities.

Thus, according to another embodiment, the invention relates to a method for evaluating the potential of a chemical entity to associate with a) a molecule or molecular complex comprising a binding pocket defined, at least in part, by structure coordinates of one or more PDK2 amino acid residues L53, Y80, S83, I111, R112, R114, H115, R154, I157, R158, I161, as described herein, or b) a homologue of said molecule or molecular complex, wherein said homologue comprises a binding pocket that has a root mean square deviation from the backbone atoms of said amino acids of not more than 2.0 (more preferably 1.5) angstroms.

This method comprises the steps of:

i) employing computational means to perform a fitting operation between the chemical entity and a binding pocket of the molecule or molecular complex; and ii) analyzing the results of the fitting operation to quantify the association between the chemical entity and the binding pocket.

The term "chemical entity", as used herein, refers to chemical compounds, complexes of at least two chemical compounds, and fragments of such compounds or complexes.

In certain embodiments, the method evaluates the potential of a chemical entity to associate with a molecule or molecular complex defined by structure coordinates of all or some of the amino acids of PDK2, as described herein, or a homologue of said molecule or molecular complex having a root mean square deviation from the backbone atoms of said amino acids of not more than 2.0 (more preferably not more than 1.5) angstroms.

In a further embodiment, the structural coordinates one of the binding pockets described herein can be utilized in a method for identifying a potential agonist or antagonist of a molecule comprising an PDK2 binding site or pocket. This method comprises the steps of:

a) using the atomic coordinates of PDK2 amino acid residues L53, Y80, S83, I111, R112, R114, H115, R154, I157, R158, I161, as described herein, with a root mean square deviation from the backbone atoms of said amino acids of not more than about 2.0 (more preferably not more than 1.5) angstroms, to generate a three-dimensional structure of molecule comprising an PDK2 binding site or pocket;

b) employing the three-dimensional structure to design or select the potential agonist or antagonist. The method further includes the optional steps of c) synthesizing the agonist or antagonist; and d) contacting the agonist or antagonist with the molecule to determine the ability of the potential agonist or antagonist to interact with the molecule.

The present inventors' elucidation of particular binding sites or pockets in the structure of PDK2 provides the necessary information for identifying and/or designing new chemical entities and compounds that may interact with PDK2, in whole or in part, and may therefore modulate (e.g., inhibit or decrease) the activity of PDK2.

The design of compounds that bind to PDK2 binding sites or pockets according to this invention generally involves consideration of several factors. First, the entity must be capable of physically and structurally associating with parts or all of an PDK2 binding site or pocket. Non-covalent molecular interactions important in this association include hydrogen bonding, van der Waals interactions, hydrophobic interactions and electrostatic interactions. Second, the entity must be able to assume a conformation that allows it to associate with an PDK2 binding site or pocket directly. Although certain portions of the entity will not directly participate in these associations, those portions of the entity may still influence the overall conformation of the molecule. This, in turn, may have a significant impact on potency. Such conformational requirements include the overall three-dimensional structure and orientation of the chemical entity in relation to all or a portion of the binding pocket, or the spacing between functional groups of an entity comprising several chemical entities that directly interact with the binding pocket or homologues thereof.

The potential inhibitory or binding effect of a chemical entity on a PDK2 binding site or pocket may be analyzed prior to its actual synthesis and testing by the use of computer modeling techniques. If the theoretical structure of the given entity suggests insufficient interaction and association between it and the target binding pocket, testing of the entity is obviated. However, if computer modeling indicates a strong interaction, the molecule may then be synthesized and tested for its ability to bind to a binding pocket. This may be achieved, e.g., by testing the ability of the molecule to inhibit PDK2 activity, e.g., using assays described herein or known in the art. In this manner, synthesis of inoperative compounds may be avoided.

A potential inhibitor of an PDK2-related binding pocket may be computationally evaluated by means of a series of steps in which chemical entities or fragments are screened and selected for their ability to associate with the PDK2-related binding pockets.

One skilled in the art may use one of several methods to screen chemical entities or fragments for their ability to associate with an PDK2 binding site or pocket (e.g., the pocket where dichloroacetate binding occurs). This process may begin by visual inspection of, for example, an PDK2 binding site or pocket on the computer screen based on the structure coordinates described herein, or other coordinates which define a similar shape generated from the machine-readable storage medium. Selected fragments or chemical entities may then be positioned in a variety of orientations, or docked, within that binding pocket as defined supra. Docking may be accomplished using software such as Quanta and DOCK, followed by energy minimization and molecular dynamics with standard molecular mechanics force fields, such as CHARMM and AMBER.

Specialized computer programs (e.g., as known in the art and/or commercially available and/or as described herein) may also assist in the process of selecting fragments or chemical entities.

Once suitable chemical entities or fragments have been selected, they can be assembled into a single compound or complex. Assembly may be preceded by visual inspection of the relationship of the fragments to each other on the three-dimensional image displayed on a computer screen in relation to the structure coordinates of the target binding pocket.

Instead of proceeding to build a compound capable of binding to a binding pocket in a step-wise fashion one fragment or chemical entity at a time as described above, inhibitory or other binding compounds may be designed as a whole or "de novo" using either an empty binding site or optionally including some portion(s) of a known inhibitor(s). There are many de novo ligand design methods known in the art, some of which are commercially available (e.g., LeapFrog, available from Tripos Associates, St. Louis, Mo.).

Other molecular modeling techniques may also be employed in accordance with this invention (see, e.g., N. C. Cohen et al., "Molecular Modeling Software and Methods for Medicinal Chemistry, J. Med. Chem., 33, pp. 883-894 (1990); see also, M. A. Navia and M. A. Murcko, "The Use of Structural Information in Drug Design", Current Opinions in Structural Biology, 2, pp. 202-210 (1992); L. M. Balbes et al., "A Perspective of Modern Methods in Computer-Aided Drug Design", in Reviews in Computational Chemistry, Vol. 5, K. B. Lipkowitz and D. B. Boyd, Eds., VCH, New York, pp. 337-380 (1994); see also, W. C. Guida, "Software For Structure-Based Drug Design", Curr. Opin. Struct. Biology, 4, pp. 777-781 (1994)).

Once a compound has been designed or selected, the efficiency with which that entity may bind to a binding pocket may be tested and optimized by computational evaluation.

Specific computer software is available in the art to evaluate compound deformation energy and electrostatic interactions. Examples of programs designed for such uses include: AMBER; QUANTA/CHARMM (Accelrys, Inc., Madison, Wis.) and the like. These programs may be implemented, for instance, using a commercially-available graphics workstation. Other hardware systems and software packages will be known to those skilled in the art.

Another technique involves the in silico screening of virtual libraries of compounds, e.g., as described herein (see, e.g., the Examples herein below). Many thousands of compounds can be rapidly screened and the best virtual compounds can be selected for further screening (e.g., by synthesis and in vitro testing). Small molecule databases can be screened for chemical entities or compounds that can bind, in whole or in part, to an PDK2 binding site or pocket. In this screening, the quality of fit of such entities to the binding site may be judged either by shape complementarity or by estimated interaction energy.

In the methods described herein, the additional steps of procuring (e.g., purchasing or obtaining from a commercial source or compound library, synthesizing, etc.) the compound and/or testing the compound in a laboratory protocol (e.g., assay, experiment, etc.) may also be included.

Finally, additional computational techniques can be used for automated structure-based optimization with software packages such as RACHEL (Tripos, Inc.). RACHEL allows a database of fragments to be screened and evaluated (i.e., scored) as each fragment is considered as an extension of the lead compound. The lead compound can then be grown in silico at user defined sites and ranked again. This approach can provide a "filtered" library of derivatives likely to have an increased affinity for the target.

The invention also provides methods for designing, evaluating and identifying compounds which bind to the aforementioned binding site/pocket. Such compounds are potential inhibitors or modulators of PDK2 activity. Other embodiments of the invention are disclosed herein.

The invention is further illustrated by the following examples which should in no way be construed as being further limiting.

EXAMPLES

Materials and Methods

Virtual Screening

The software package of DOCK6 (Ewing et al. 2001) was used for in silico screening of ~140,000 compounds available from the National Cancer Institute, Developmental Therapeutics Program. The structure coordinates and chemical information for each compound were processed either using DOCK accessory programs including GRID (Irwin and Shoichet 2005). Molecular docking was performed by parallel processing using 16 processors on the linux cluster at the High Performance Computing Center, University of Florida.

The grid-based scoring system was used for scoring with the non-bonded force field energy function implemented in DOCK. A standard 6-12 Lennard-Jones potential was used to evaluate van der Waals contacts. Spheres were generated by SPHGEN_CPP (Kuntz et al. 1982) and clusters were edited by hand to target specific sites on the molecular surface of PDK2.

Data Analysis

Data were analyzed with one-way ANOVA or Student's t-test ((JMP 7.0®, SAS Institute Inc., Cary, N.C.). A p value $\leq 0.05$ was considered statistically significant.

Materials and Methods

Cell Culture, Treatment and Plasmids

Primary cultures of fibroblasts were established from skin biopsies of three healthy subjects and three patients (one male and two females) with PDH E1α deficiency. The patients had the following mutations in the PDHA1 gene: patient 1, c.1163_1166dupAAGT in exon 11; patient 2, c.904C>T in exon 10; and patient 3, c.642G>T in exon 7. Cells were cultured as monolayers in T-flasks in complete Dulbecco's Modified Eagle's Medium (Sigma, St. Louis, Mo.). The medium contained 25 mM glucose and was supplemented with 20% fetal bovine serum (Hyclone, Logan, Utah), 1% penicillin/streptomycin solution (10,000 U of penicillin and 10 mg/ml of streptomycin) (Sigma, St. Louis, Mo.), 1% insulin-transferrin solution (0.5 mg/ml), 0.2% fibroblast growth factor solution (1 µg/ml) and 1% L-glutamine solution (0.1 M). Cultures were maintained at 37° C. in a humidified 5% $CO_2$/95% air atmosphere. In some experiments, cells were exposed for the final 24 hours of culture to media containing 5 mM DCA (sodium salt; TCI Organics, Portland, Oreg.).

Cells from the human embryonic kidney cell line 293 (HEK 293) were maintained at 37° C. in a 5% $CO_2$ atmosphere in Iscove's-modified Dulbecco's medium (IMDM) media supplemented with 10% newborn bovine serum and 1% penicillin/streptomycin solution (10,000 U of penicillin and 10 mg/ml of streptomycin; Sigma, St. Louis, Mo.).

Construction of the Recombinant AAV Vector

Standard cloning techniques were used for constructing all recombinant AAV-based plasmids. The University of Florida Powell Gene Therapy Center produced conventional rAAV (ssAAV) serotype 2 vectors for this study and scAAV serotype vectors were packaged in the Division of Cellular and Molecular Therapy. Briefly, virus production included use of the helper/packaging plasmid that supplies all the necessary helper functions as well as rep and cap in trans. The vector plasmid pCBA-PDH-EGFP was cotransfected with pDG into ~70-95% confluent HEK 293 cells by calcium phosphate precipitation. Recombinant AAV was prepared by iodixanol centrifugation and heparin-column purification. Physical titer (genome number) was determined by dot blot. The titer used was $10^{12}$ particles/ml for ssAAV-PDH-GFP. For scAAV vectors, each cassette was composed of AAV inverted terminal repeats (ITRs) with a the chicken β-actin (CBA) promoter driving the EGFP gene. Human PDHA1 gene insert was derived from plasmid pCBA-PDH essentially as described in Curr. Gene Ther. 3:239-245 (2003) or Hum. Gene Ther. 11:2067-2078 (2000). Briefly, pCBA-PDH was digested with NotI and EcoRI to release a 1191-bp fragment and pdsCBA-EGFP was digested with StuI and HindIII. The vector and insert were treated with the Klenow fragment of *Escherichia coli* DNA polymerase I and then blunt-end ligated. After transformation, the plasmid, pscAAV-CBA-PDH, with the right orientation and ITRs were selected for packaging scAAV vectors.

Recombinant AAV Vector-Mediated Transduction Assays

Approximately $2 \times 10^5$ cells were plated in each well in 12-well plates, respectively, and incubated at 37° C. for 12 hrs. Cells were washed once with serum-free IMDM and then either mock-infected or infected with scAAV1-EGFP using serotypes AAV1-3, 5-7 and 9, at a 200 particles per cell. Cells were observed under a Zeiss Axiovert 25 fluorescence microscope (Carl Zeiss, Inc., Thornwood, N.Y.) 3 days after infection. The viral transduction efficiency was measured by GFP imaging, using images from three visual fields and was quantitated by ImageJ (NIH, Bethesda, Md.).

For ssAAV transduction experiments, cells were coinfected with adenovirus and ssAAV vectors. Cells were grown to approximately 90% confluency in 6-well plates ($10^5$ cells/well). They were infected with the ssAAV vector at a concentration of 10,000 vector particles per cell (PPC) and with 1 µl of adenovirus/per well ($10^9$ particles/ml). Cells were then cultured under normal growth conditions and monitored for GFP expression.

Western Immunoblotting

Total protein concentrations were determined using the Bio-Rad protein assay kit. Protein lysates from each cultured cell line were electrophoresed on 10% polyacrylamide-SDS gels. Following transfer to an PVDF membrane (Millipore, Bedford, Mass.), the membrane was blocked at room temperature (RT) for 1 hr with 5% nonfat dry milk in 1× Tris-buffered saline (TBS; 20 mM Tris-HCl, pH 7.5, 150 mM NaCl), and 0.05% Tween 20, then incubated with 6 µg/ml of E1α, E1β, E2 and E2/E3 bp mAbs (MitoSciences Inc., Eugene, Oreg.) for 1 hr at RT. Subsequently, the secondary antibody, a horseradish peroxidase-conjugated bovine anti-mouse IgG (Santa Cruz Biotechnology, Inc., Santa Cruz, Calif.), was added at a 1:2000 dilution for 1 hour at RT. Signals were detected using a chemiluminescence luminol reagent (Santa Cruz Biotechnology, Inc., Santa Cruz, Calif.) according to the instructions provided by the manufacturer.

PDH Activity

PDH complex activity was measured by the rate of $^{14}C$ formation from [1-$^{14}C$]-labeled pyruvate, as described in *Mitochondrion* 6:126-135 (2006) or *Mitochondrion*. 7: 253-259 (2007). Fibroblasts harvested by trypsinization from a confluent T-75 flask were washed in phosphate-buffered saline (PBS) and resuspended in PBS containing the serine protease inhibitors leupeptin and phenylmethylsulfonyl fluoride (PMSF). Cells were incubated for 15 min at 37° C. with DCA. Reactions were halted by addition of a stop solution (25 mM NaF, 25 mM EDTA, 4 mM dithiothreitol, 40% ethanol), and cells were lysed by repeated freezing and thawing. Sixteen aliquots of each fibroblast sample were assayed in test tubes for enzyme activity. Four samples that contained only lysate and water and four samples that also contained thiamine pyrophosphate and coenzyme A were assayed at reaction times of 5 and 10 min. A $^{14}$C-labeled pyruvate aliquot of known specific activity was added to the cell lysates and the test tubes were immediately closed with a rubber stopper. The stopper was outfitted with a center well (Kimble-Kontes, Vineland, N.J.) that contained 1 cm$^2$ chromatography paper soaked with 100 μl hyamine hydroxide. Reactions were halted by adding stopping buffer. The $^{14}$CO2 evolved due to PDH-mediated catalysis and trapped in the paper was determined by liquid scintillation. PDH specific activity was expressed as nmol $^{14}$CO2 produced/min/mg protein. Excess cell lysate was used to determine total protein.

Example 1

Approximately 140,000 compounds were virtually screened with DOCKv5.2 (Ewing et al. 2001) and ranked by energy score. This computer database was prepared with DOCK accessory software (SF2MOL2, UCSF) and Sybyl (Tripos, Inc.).

The crystal structure of PDK2 was obtained from the Protein Data Bank (PDB ID: 2BU8) (www.pdb.org).

We first predicted the three-dimensional structure of PDK2 (SWISS-MODEL) based on the solved crystal structure of PDK2. The docking site was selected based on its unique specificity to dichloroacetate (DCA) binding, and on characteristics favorable for small molecule binding. The DCA binding pocket was identified and its molecular surface was defined to provide the basis for docking of small drug-like molecules. (Connolly, M. L. 1983. Analytical molecular surface calculation. *Journal of Applied Crystallography.* 16: 548-558). The binding site was defined using the SPHGEN software program and filtered through the CLUSTER program. (Ewing et al., 2001. DOCK 4.0: search strategies for automated molecular docking of flexible molecule databases. *J. Comput.-Aided Mol. Des.* 15: 411-428).

Example 2

The fifteen compounds that had the highest scores for potential PDK2 binding were selected and screened for their potential activities for inhibition of cancer cell growth. The compounds were obtained from NCI Developmental Therapeutics Program.

The compounds (predicted to interact with PDK2) were tested in human fibroblast cultures from three healthy subjects for their effect on PDH activity. DCA and dimethyl sulfoxide (DMSO) were used as positive and vehicle controls, respectively. Drugs were dissolved in DMSO and were used at maximum feasible dose in initial studies (0.25 to 2 mM). For dose-response experiments, concentrations used were: 0.01, 0.05, 0.1, 0.5, 1, and 5 mM. DCA was used as positive control. Cells were exposed to media with DCA, NCI compounds or DMSO vehicle for the final 24 h of culture.

Primary cultures of fibroblasts were grown at 37° C. in a humidified 5% $CO_2$/95% air atmosphere in DMEM supplemented with 20% (v/v) FBS, 100 U/mL penicillin, 100 μg/mL streptomycin, and 6 mM L-glutamine.

Cell lysates treated with DCA or NCI compounds were incubated in a reaction buffer that contained [1-$^{14}$C]-pyruvate. PDH activity was measured by quantitation of liberated $^{14}$CO$_2$. (Han et al., 2007. Down-regulation of rat pyruvate dehydrogensae E1a gene by self-complementary adeno-associated virus-mediated small interfering RNA delivery. *Mitochondrion.* 7: 253-259). Each sample was run in triplicate, with appropriate blanks.

PDH activity, measured by the rate of $^{14}$CO$_2$ formation from [1-$^{14}$C]-labeled pyruvate, was run in triplicate per cell line. DCA increased PDH enzymatic activity by 180±17 to 195±6% compared to the DMSO control (p≦0.05). Six of the drugs that we tested also significantly increased PDH activity compared to DMSO control (150±5, 170±17, 164±14, 189±40, 174±12, and 186±6%). Dose-response studies (0.01 to 5 mM) for the compounds that increased PDH activity suggest that compounds 10 and 14 may be more potent than DCA in improving PDH activity at the lowest concentration tested (0.01 μM).

Example 3

Figure 3:
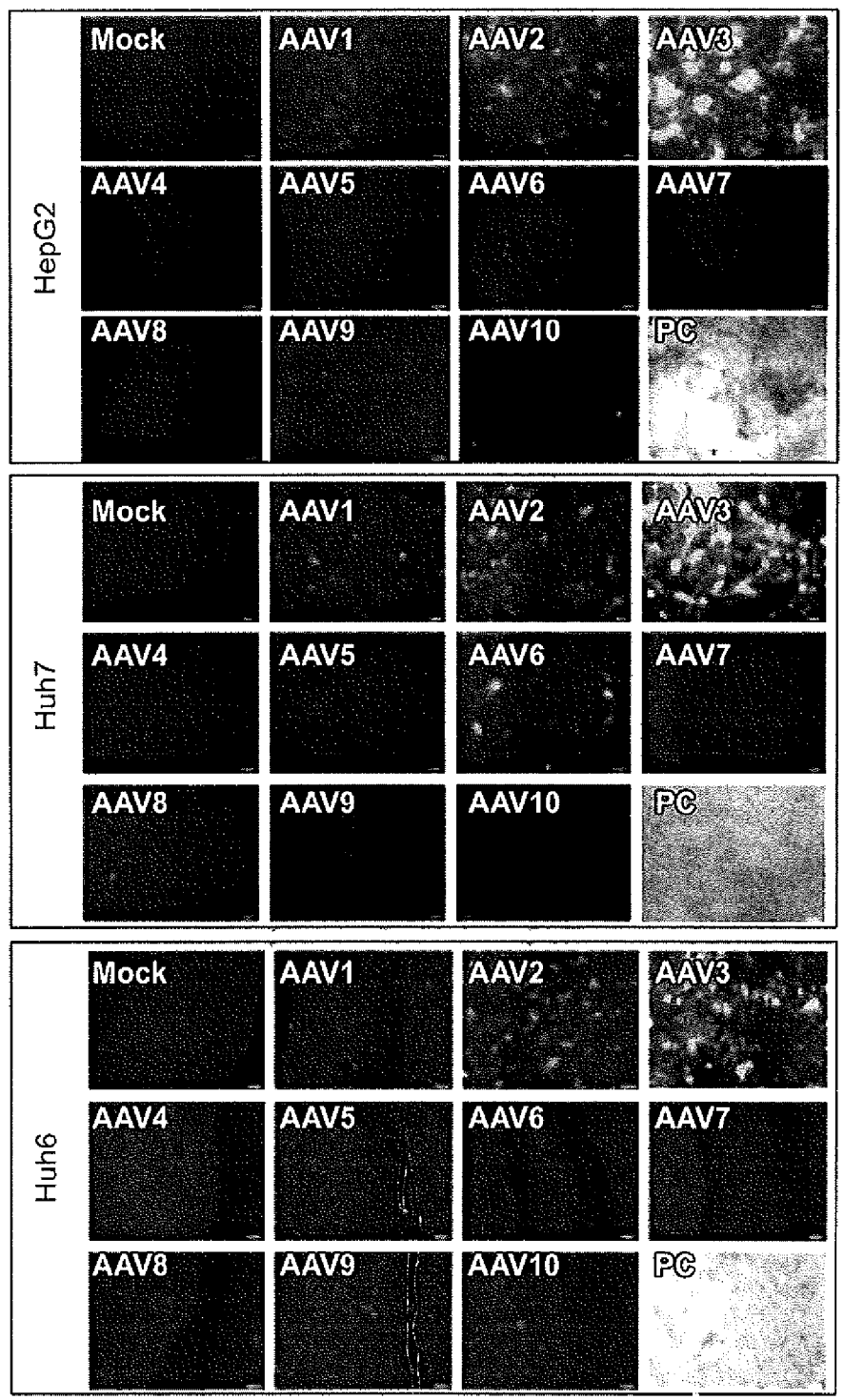
FIG. 3 shows that AAV3 serotype vectors are the most efficient in transducing human HCC and HB cells in vitro. Transduction efficiency of recombinant AAV-CBAp-EGFP serotype vectors 1 through 10 in human HCC (HepG2 and Huh7) and HB (Huh6) cell lines. Equivalent numbers of cells were either mock-infected or infected with each serotype vector under identical conditions, and transgene expression was visualized under a fluorescent microscope.

AAV3 serotype vectors efficiently transduce human hepatocellular carcinoma and hepatoblastoma cells. Two human hepatocellular carcinoma (HCC) cell lines, HepG2 and Huh7, and a human hepatoblastoma (HB) cell line, Huh6, were transduced with recombinant self-complementary adeno-associated virus (scAAV) serotype vectors 1 through 10 containing the chicken β-actin promoter (CBAp)-driven enhanced green-fluorescent protein (EGFP) gene. Cells were either mock-infected or infected with ~1,000 AAV vector particles/cell under identical conditions, and visualized under a fluorescent microscope 96 hrs post-infection. These results, shown in FIG. 3, indicate that of the 10 serotypes, AAV3 is by far the most efficient in transducing HCC and HB cell lines in vitro. Representative phase-contrast (PC) images are also shown.

Example 4

Figure 4:
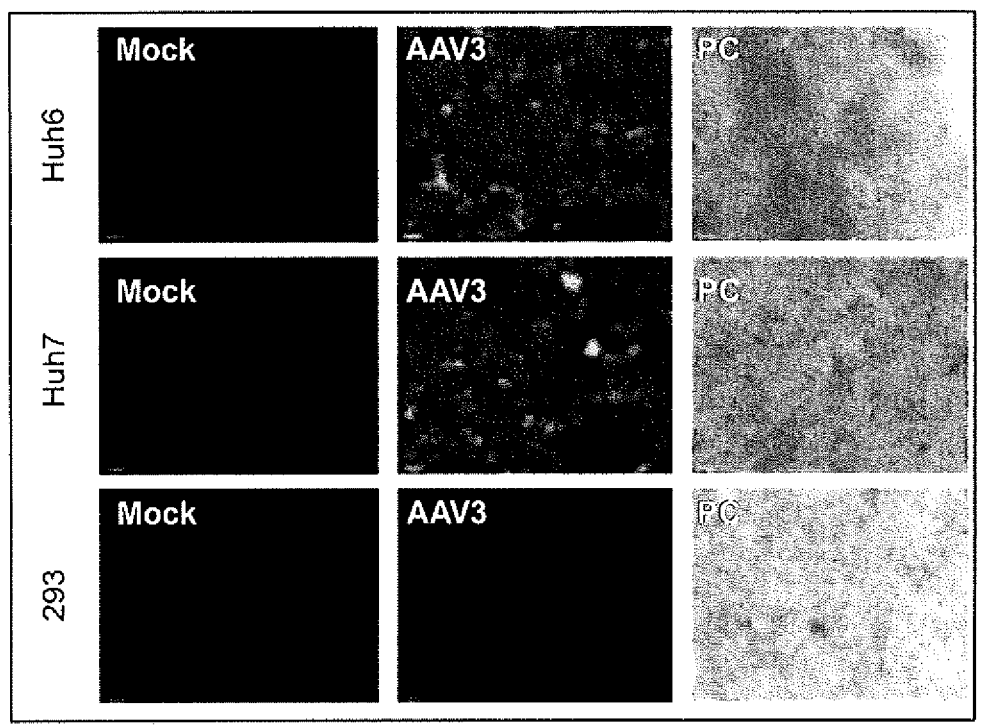
FIG. 4 shows that AAV3 vector-mediated transgene expression from the AFP promoter is restricted to HCC and HB cells. Transgene expression from the AFP promoter mediated by AAV3 serotype vectors in human HCC (Huh7) and HB (Huh6) cells and embryonic kidney (293) cells. Equivalent numbers of cells were either mock-infected or infected with AAV3-AFPp-EGFP serotype vectors under identical conditions, and transgene expression was visualized under a fluorescent microscope.

HCC- and HB-specific transgene expression can be achieved by AAV3 serotype vectors. HCC and HB cell lines as well as a human embryonic kidney cell line, 293, were transduced with ~2,000 particles/cells of recombinant AAV3 serotype vectors containing the EGFP gene under the control of the human α-feto-protein (AFP) promoter, expression from which is known to be restricted to HCC and HB cell lines. FIG. 4 shows that AAV3-AFPp-EGFP vector-mediated transgene expression indeed occurs in HCC and HB, but not in 293 cells.

Example 5

Figure 5:
FIG. 5 shows that primary human hepatocytes are transduced very efficiently by AAV3 serotype vectors. Transduction efficiency of recombinant AAV3 serotype vectors in primary human hepatocytes. Equivalent numbers of cells were either mock-infected or infected with AAV3-CBAp-EGFP vectors under identical conditions, and transgene expression was visualized under a fluorescent microscope.

AAV3 vectors efficiently transduce primary human hepatocytes in vitro. AAV3-CBAp-EGFP vectors were also evaluated for their ability to transduce primary human hepatocytes in vitro. Equivalent numbers of cells were either mock-infected or infected with ~50,000 AAV3 vector particles/cell under identical conditions, and visualized under a fluorescent microscope 48 and 72 hrs post-infection. These results, shown in FIG. 5, indicate that AAV3 vectors indeed transduce primary human hepatocytes very efficiently.

Example 6

Figure 6:
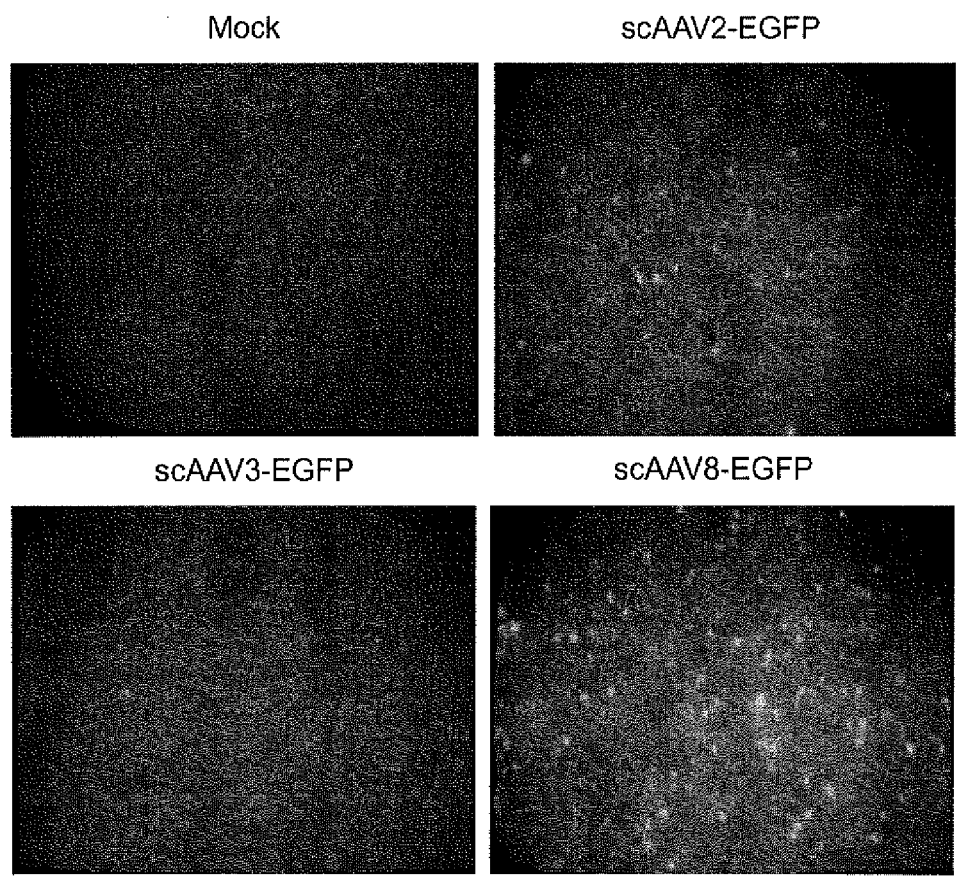
FIG. 6 illustrates that AAV3 vectors do not transduce primary mouse hepatocytes very efficiently in vivo. Transduction efficiency of recombinant AAV serotype vectors 2, 3, and 8 in mouse hepatocytes. Equivalent numbers of each serotype vectors were injected via the tail-vein in C57BL/6 mice under identical conditions, and 8-weeks post-injections, transgene expression in the liver lobes was visualized under a fluorescent microscope.

AAV3 vectors fail to efficiently transduce primary murine hepatocytes in vivo. In order to test the efficacy of recombinant AAV3 serotype vectors in specifically targeting human liver cancer cells in a mouse xenograft model in vivo, it was essential to evaluate the potential of these vectors to transduce primary murine hepatocytes in vivo. Approximately 1×10$^{10}$ vector genomes (vgs) of scAAV3-CBAp-EGFP vectors were injected via the tail-vein into normal C57BL/6 mice. Mock-injected, or mice injected with equivalent vgs of scAAV2-CBAp-EGFP and scAAV8-CBAp-EGFP serotype vectors were used as appropriate negative and positive controls, respectively. AAV2 and AAV8 vectors are known to transduce murine hepatocytes very efficiently (AAV8>AAV2). Liver sections were obtained 8-weeks post-injections, and visualized under a fluorescent microscope. These results, shown in FIG. 6, indicate that whereas efficient transduction of primary murine hepatocytes occurs by AAV8, followed by AAV2 vectors, as expected, AAV3 vector-mediated transduction is largely inefficient. Based on these studies, we anticipate that with the combined use of AAV3 serotype vectors containing the AFPp and the PDH E1α gene, it would be feasible to specifically eliminate HCC and HB cells in a mouse xenograft model of human liver cancer, prior to the potential use of this strategy in targeting hepatocellular carcinoma and hepatoblastoma in humans.

The disclosures of each and every patent, patent application and publication cited herein are hereby incorporated herein by reference in their entirety.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Although the invention has been disclosed with reference to specific embodiments, it is apparent that other embodiments and variations of the invention may be devised by others skilled in the art without departing from the true spirit and scope of the invention. The sentences are intended to be construed to include all such embodiments and equivalent variations.

What is claimed is:

1. A method of treating a subject suffering from or susceptible to a cell proliferation related disorder or disease, the method comprising administering to a subject in need thereof a therapeutically effective amount of a pyruvate dehydrogenase kinase 2 (PDK2) enzyme inhibitor that is selected from the group consisting of 2-methylbut-2-enedioic acid (Compound 10), 2-(3H-imidazol-4-yl)acetic acid (Compound 14), 2-(carbamoylamino)-2-methoxyacetic acid (Compound 17), (E)-3-chlorobut-2-enoic acid (Compound 18), thiadizaole-4-carboxylic acid (Compound 19), 4-amino-6-oxo-3H-pyrimidine-2-carboxylic acid (Compound 20), (Z)-3-bromoprop-2-enoic acid (Compound 21), (Z)-but-2-enoic acid (Compound 24), and salts thereof, to thereby treat the subject suffering from or susceptible to a cell proliferation related disorder or disease.

2. The method of claim 1, wherein the PDK2 inhibitor inhibits mitochondrial PDK.

3. The method of claim 2, wherein the PDK2 inhibitor compound is demonstrated to bind to PDK2 at an amino acid sequence comprising PDK2 amino acid residues L53, Y80, S83, I111, R112, R114, H115, R154, I157, R158, I161 of full-length PDK2 human enzyme.

4. The method of claim 1, wherein the subject is identified as in need of treatment by administration of an PDK2 inhibitor compound.

5. The method of claim 1, wherein the subject is identified as in need of treatment by administration of a PDK2 inhibitor compound that is demonstrated to bind to PDK2 at an amino acid sequence comprising PDK2 amino acid residues L53, Y80, S83, I111, R112, R114, H115, R154, I157, R158, K161 of full-length PDK2 human enzyme.

6. The method of claim 1, wherein a pyruvate dehydrogenase complex (PDC) is activated via PDK2 inhibition.

7. The method of claim 1, wherein the PDK2 inhibitor compound is a compound of Table 1 that was demonstrated to increase pyruvate dehydrogenase complex (PDC) activity in human fibroblast cultures.

8. The method of claim 1, further comprising administration to the subject of a nucleic acid that encodes pyruvate dehydrogenase (PDH) E1 alpha.

9. The method of claim 8, wherein the nucleic acid is transferred using an adeno-associated virus (AAV) serotype vector.

10. The method of claim 9, wherein the AAV serotype vector is AAV serotype 3.

11. The method of claim 8, where the subject is a human.

* * * * *